(12) United States Patent
Lai et al.

(10) Patent No.: US 10,138,300 B2
(45) Date of Patent: Nov. 27, 2018

(54) ANTI-VEGFR ANTIBODY AND USES THEREOF

(71) Applicant: DEVELOPMENT CENTER FOR BIOTECHNOLOGY, New Taipei (TW)

(72) Inventors: Jiann-Shiun Lai, New Taipei (TW); Li-Shuang Ai, New Taipei (TW); Yan-Da Lai, New Taipei (TW); Yen-Yu Wu, New Taipei (TW); Yi-San Tsai, New Taipei (TW); Yi-Jiue Tsai, New Taipei (TW); Juo-Yu Huang, New Taipei (TW); Cheng-Chou Yu, New Taipei (TW); Chuan-Lung Hsu, New Taipei (TW); Chien-Tsun Kuan, New Taipei (TW); Szu-Liang Lai, New Taipei (TW); Li-Ya Wang, New Taipei (TW)

(73) Assignee: DEVELOPMENT CENTER FOR BIOTECHNOLOGY, New Taipei (TW)

(*) Notice: Subject to any disclaimer, the term of this patent is extended or adjusted under 35 U.S.C. 154(b) by 0 days.

(21) Appl. No.: 15/640,935

(22) Filed: Jul. 3, 2017

(65) Prior Publication Data

US 2018/0186884 A1 Jul. 5, 2018

Related U.S. Application Data

(63) Continuation of application No. 15/393,534, filed on Dec. 29, 2016.

(51) Int. Cl.
| | | |
|---|---|---|
| *C07K 16/28* | (2006.01) | |
| *C07K 16/30* | (2006.01) | |
| *G01N 33/74* | (2006.01) | |
| *A61K 51/10* | (2006.01) | |
| *A61K 31/4439* | (2006.01) | |
| *C07K 14/71* | (2006.01) | |
| *C07K 16/00* | (2006.01) | |
| *A61K 47/68* | (2017.01) | |
| *A61K 47/48* | (2006.01) | |
| *A61K 39/00* | (2006.01) | |

(52) U.S. Cl.
CPC ...... *C07K 16/2863* (2013.01); *A61K 31/4439* (2013.01); *A61K 47/48561* (2013.01); *A61K 47/6803* (2017.08); *A61K 47/6849* (2017.08); *A61K 51/1027* (2013.01); *A61K 51/1096* (2013.01); *C07K 14/71* (2013.01); *C07K 16/005* (2013.01); *C07K 16/2818* (2013.01); *C07K 16/30* (2013.01); *G01N 33/74* (2013.01); *A61K 2039/505* (2013.01); *A61K 2039/507* (2013.01); *C07K 2317/24* (2013.01); *C07K 2317/34* (2013.01); *C07K 2317/55* (2013.01); *C07K 2317/56* (2013.01); *C07K 2317/565* (2013.01); *C07K 2317/622* (2013.01); *C07K 2317/76* (2013.01); *C07K 2317/77* (2013.01); *C07K 2317/92* (2013.01); *G01N 2333/71* (2013.01)

(58) Field of Classification Search
CPC ............ C07K 16/2863; C07K 16/30; C07K 2317/565; C07K 2317/56; C07K 2317/24; A61K 47/48561; A61K 31/4439; A61K 51/1096; G01N 33/74; G01N 2333/71
See application file for complete search history.

(56) References Cited

U.S. PATENT DOCUMENTS

| | | |
|---|---|---|
| 7,138,272 B1 | 11/2006 | Cichutek et al. |
| 2003/0108545 A1 | 6/2003 | Rockwell et al. |
| 2003/0235584 A1 | 12/2003 | Kloetzer et al. |
| 2004/0137513 A1 | 7/2004 | Devaux et al. |
| 2009/0022716 A1 | 1/2009 | Rockwell et al. |
| 2009/0104215 A1 | 4/2009 | Ekiel et al. |
| 2010/0129362 A1 | 5/2010 | Law et al. |
| 2010/0226923 A1 | 9/2010 | Rao et al. |
| 2013/0243795 A1 | 9/2013 | Chen et al. |

FOREIGN PATENT DOCUMENTS

| | | |
|---|---|---|
| JP | 2007-202443 A | 8/2007 |
| TW | 201718641 A | 6/2017 |
| WO | 2015/164745 A1 | 10/2015 |
| WO | 2017004254 A1 | 1/2017 |

OTHER PUBLICATIONS

English translation of the abstract for TW201718641A.
Search Report issued in co-pending Taiwan Patent Application No. 106121860.
English Translation of the Taiwan Search Report.
International Search Report and Written Opinion of the International Searching Authority dated Nov. 21, 2017 for International Application No. PCT/US17/40584.
espacenet English abstract of JP 2007-202443 A.
Kendrew, J., et al., "An Antibody Targeted to VEGFR-2 Ig Domains 4-7 Inhibits VEGFR-2 Activation and VEGFR-2-Dependent Angiogenesis without Affecting lLigand Binding", Molecular Cancer Therapeutics, vol. 10, No. 5, May 2011, pp. 770-783.

(Continued)

*Primary Examiner* — Ruixiang Li
(74) *Attorney, Agent, or Firm* — Ladas & Parry LLP

(57) ABSTRACT

The present invention relates to an antibody or antigen-binding fragment thereof that bind human vascular endothelial growth factor receptor 2 (VEGFR-2). The present invention also relates to a method for inhibiting VEGFR-2-mediated signaling in a subject in need, a method for treating diseases and/or disorders caused by or related to VEGFR-2 activity and/or signaling in a subject afflicted with the diseases and disorders, a method for treating tumor in a subject afflicted with the tumor, a method for inhibiting cell proliferation of endothelial cells in a subject in need, and a method for detecting human vascular endothelial growth factor receptor in a sample.

10 Claims, 16 Drawing Sheets

Specification includes a Sequence Listing.

(56) References Cited

OTHER PUBLICATIONS

UniProtKB Accession No. AOA062VQT6, Uncharacterized protein M1crobacteriun1 sp CH12i, Sep. 3, 2014. [obtained online Oct. 17, 2017 at http://www.uniprotorg/uniprot!AOA062VQT6] residues 102-109.
Genbank Accession No. U39824 "Mus musculus strain A.TH 1g kappa chain mRNA, partial cds" Nov. 29, 1995 [obtained online 10117/2017 at https://www.ncbi .nlm.nih.gov/nuccore/1079728] entire sequence.

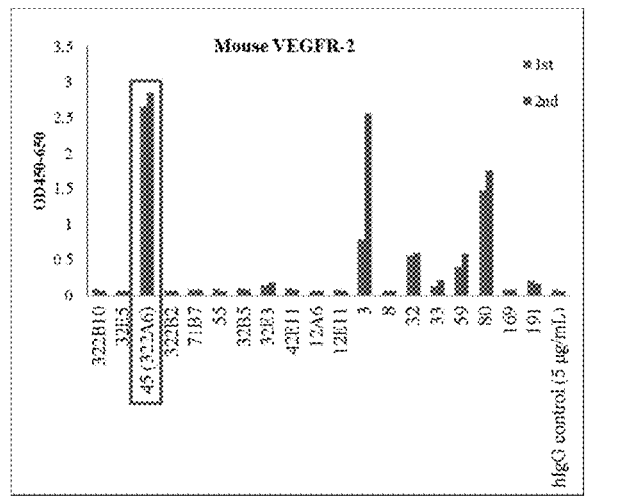
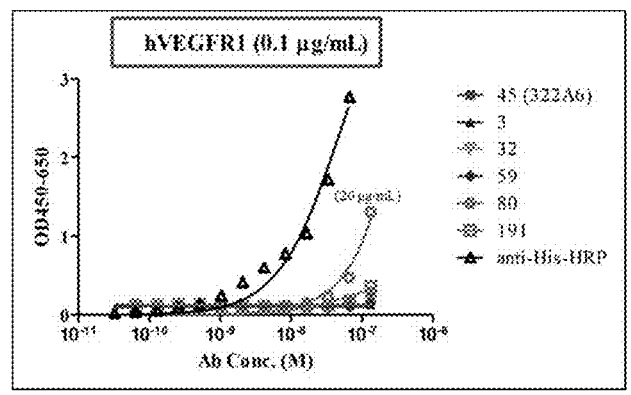
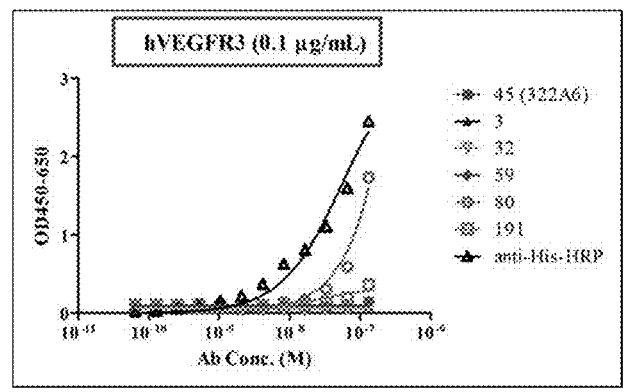
FIG. 1

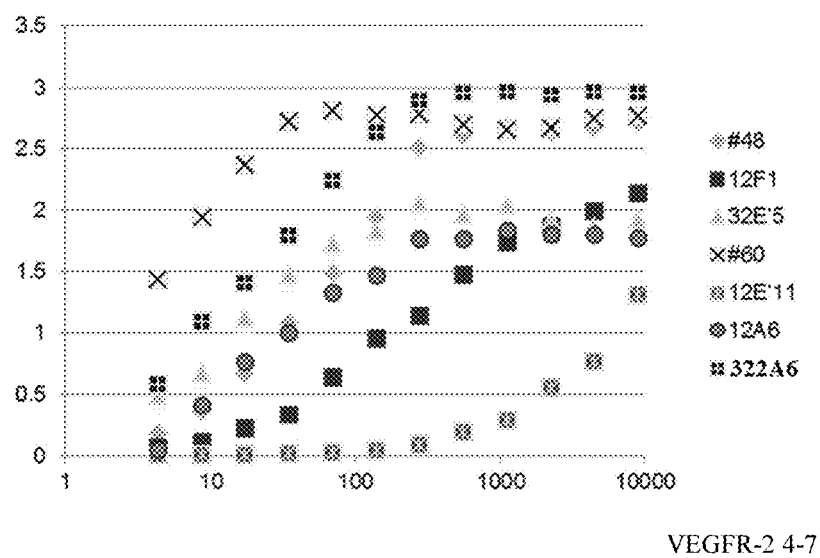
VEGFR-2 4-7 His
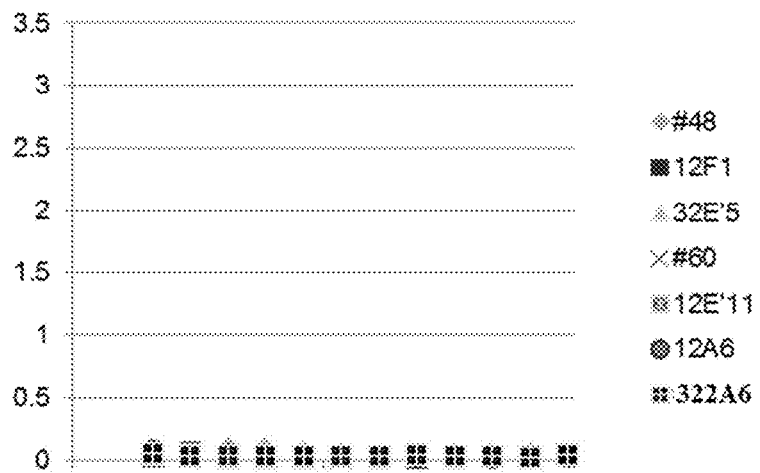
VEGFR-2 1-3 His
FIG. 2

322A6 epitopes

Mut6: S(711)
Mut8: KD(716.717)
Mut10: RR(725,726)

12A6 epitopes

Mut2: LD(606,607)
Mut4: RKT(647,648,649)

Domain 6 (551-660):

PEITLQPDMQ-PTEQESVSLWCTADRSTFENLTWYKLGPQPLPIHVGELPT

PVCK(604)NLD(606.607)TLWKLNATMFSNSTNDILIMELKNASLQDQGDYVCLAQ(645)
    Mut1    Mut2                                                       Mut3

DRKT(647.648.649)KK(651)RHCVVRQLT
    Mut4          Mut5

Domain 7 (667-753)

PTITGNLENQTTSIGESIEVSCTASGNPPPQIMW

FKDNETLVEDS(711)GIV(714)LKD(716.717)GNRN(720.721)LTIRR(725.726)V
          Mut6     Mut7    Mut8     Mut9     Mut10
RKEDEGLYTCQACSVLGCAKVEAFFI

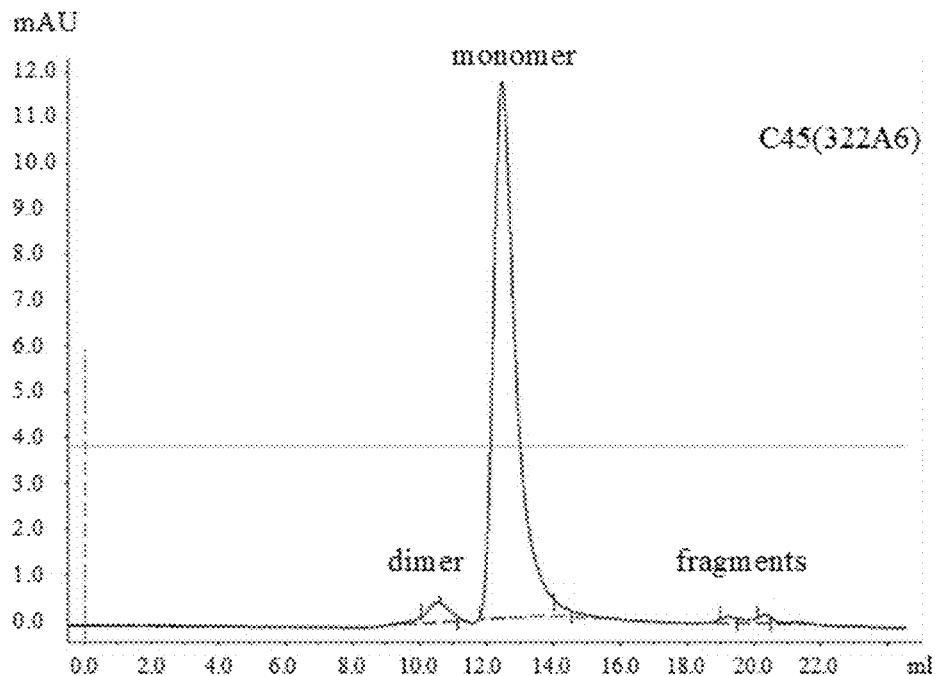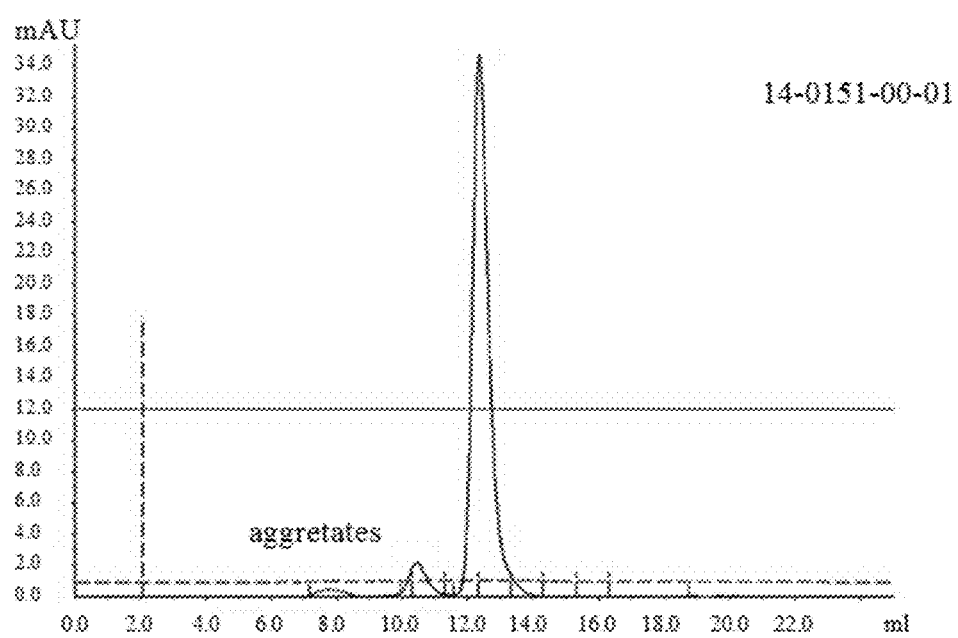
FIG. 8

- HUVEC cell (P=n+1): 1*10⁵ cell
- 1 Ab: c45(322A6)/ADC: 4 µg
- 2Ab: α-human IgG Kappa-FITC: 1:200 (Bethyl, Cat. Cat.A80-115F)

- Seeding 4000 cells/ well/96-well plate
- Incubation period: 72 hrs
- Max Ab conc.: 50 µg/mL

1121
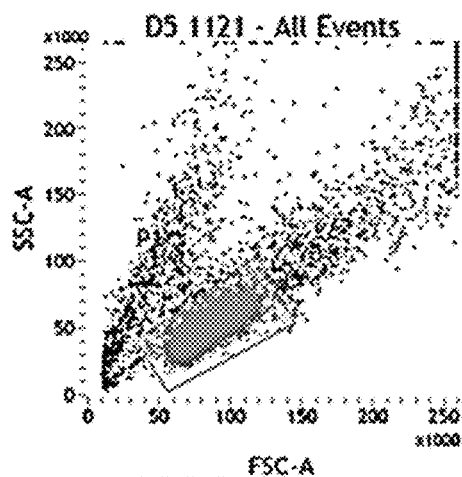 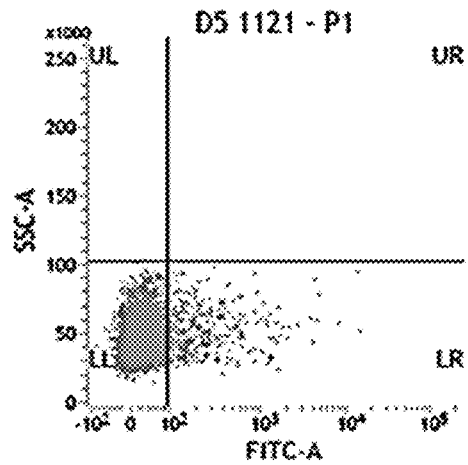
12A6
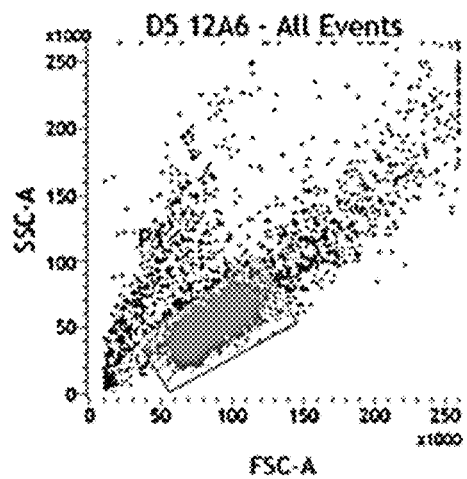 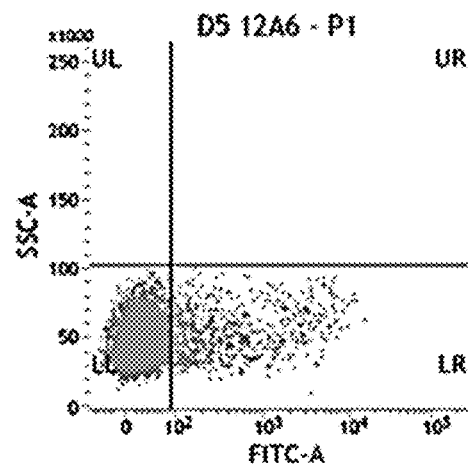
322A6
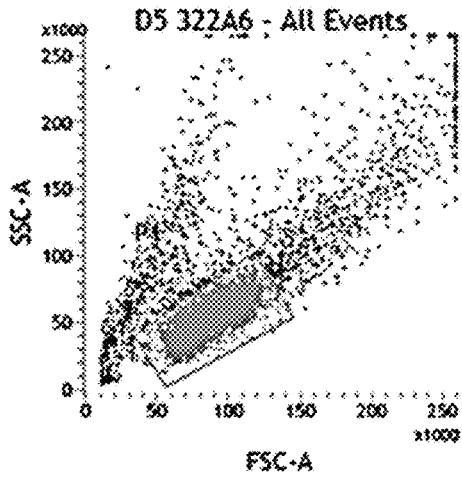 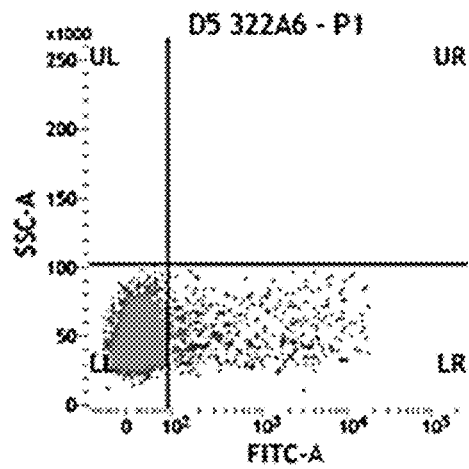
FIG. 12

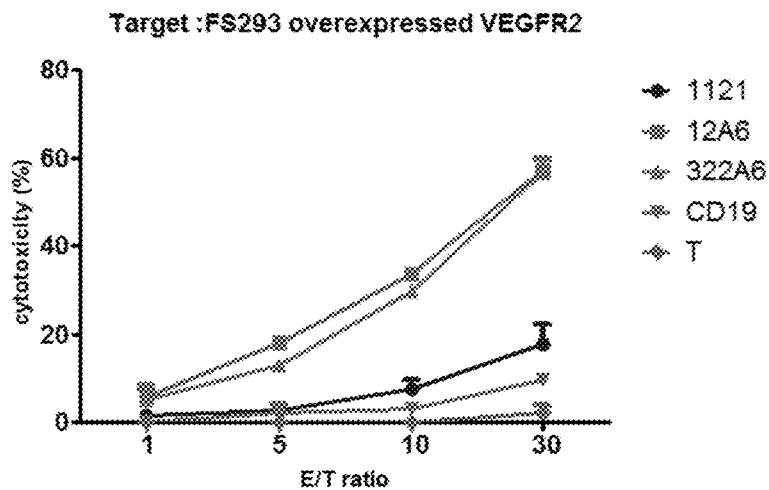
FIG. 13
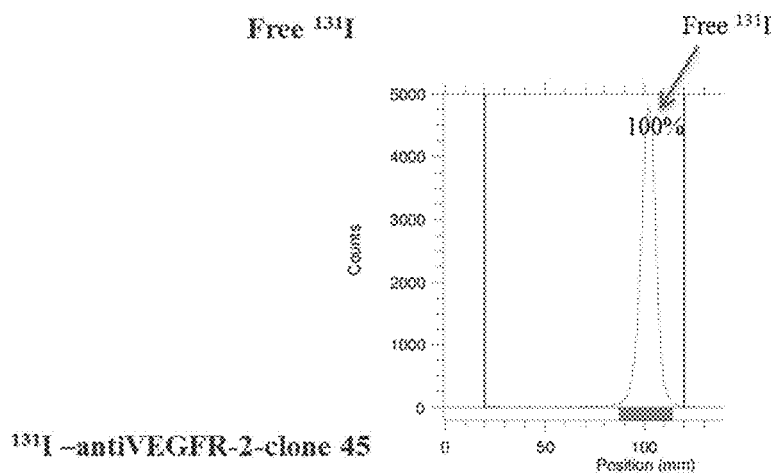
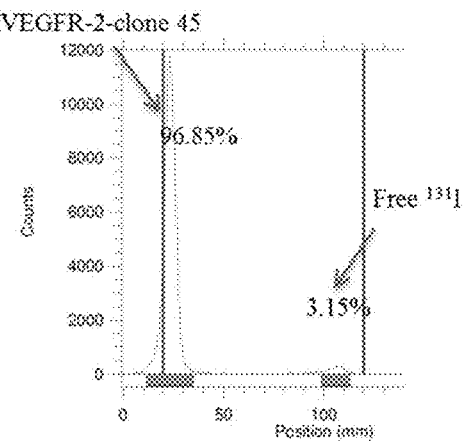
FIG. 14

```
Kabat        1        5       10       15       20          CDR-1          35       40
M            DIVLTQSPASLAVSLGQRATISC[RASKSVSTSGYSYMH]WYQQKP
Hd           DIQMTQSPSSLSASVGDRVTITC[RASKSVSTSGYSYMH]WYQQKP Kabat               45          CDR-2            60      65      70      75       80       85
M            GQPPKLLIY[LASNLES]GVPARFSGSGSGTDFTLNIHPVEEEDAATY
Hd           GKAPKLLIY[LASNLES]GVPSRFSGSGSGTDFTLTISSLQPEDFATY Kabat               CDR-3         100    104
M            YC[QHSRELPWT]FGGGTKLEIKR
Hd           YC[QHSRELPWT]FGQGTKVEIKR
```

FIG. 16

```
Kabat        1        5       10       15       20      25        CDR-1         36       40
M            EVQLQQSGPQLVRPGASAKISCKAS[GYAFTTYWMH]WVKQRPGQG
Hu           QVQLVQSGAEVKKPGASVKVSCKAS[GYTFTSYYMH]WVRQAPGQG
HuB1         QVQLVQSGAEVKKPGASVKVSCKAS[GYAFTTYWMH]WVRQAPGQG Kabat              45              CDR-2              66      70       75      80 82ABC
M            LEWIG[MIDPSDSETKLNQRFKG]KATLTVDKSSSTAYMQLSSPTS
Hu           LEWMG[MIDPSDSETKLNQRFKG]RVTMTRDTSTSTVYMELSSLRS
HuB1         LEWIG[MIDPSDSETKLNQRFKG]KATLTVDKSTSTAYMELSSLRS
                  48                          6667 69 71 73     76

Kabat        85      90  9394    CDR-3          105     110
M            EDSAVYYCAR[DVRGNFDV]WGAGTTVTVSS
Hu           EDTAVYYCAR[DVRGNFDV]WGQGTLVTVSS
HuB1         EDTAVYYCAR[DVRGNFDV]WGQGTLVTVSS
```

FIG. 17

SEQUENCE LISTING

<160> NUMBER OF SEQ ID NOS: 27

<210> SEQ ID NO 1
<211> LENGTH: 764
<212> TYPE: PRT
<213> ORGANISM: Homo sapiens

<400> SEQUENCE: 1

```
Met Gln Ser Lys Val Leu Leu Ala Val Ala Leu Trp Leu Cys Val Glu
1               5                   10                  15

Thr Arg Ala Ala Ser Val Gly Leu Pro Ser Val Ser Leu Asp Leu Pro
            20                  25                  30

Arg Leu Ser Ile Gln Lys Asp Ile Leu Thr Ile Lys Ala Asn Thr Thr
        35                  40                  45

Leu Gln Ile Thr Cys Arg Gly Gln Arg Asp Leu Asp Trp Leu Trp Pro
    50                  55                  60

Asn Asn Gln Ser Gly Ser Glu Gln Arg Val Glu Val Thr Glu Cys Ser
65                  70                  75                  80

Asp Gly Leu Phe Cys Lys Thr Leu Thr Ile Pro Lys Val Ile Gly Asn
                85                  90                  95

Asp Thr Gly Ala Tyr Lys Cys Phe Tyr Arg Glu Thr Asp Leu Ala Ser
            100                 105                 110

Val Ile Tyr Val Tyr Val Gln Asp Tyr Arg Ser Pro Phe Ile Ala Ser
        115                 120                 125

Val Ser Asp Gln His Gly Val Val Tyr Ile Thr Glu Asn Lys Asn Lys
    130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Lys Lys Gly Phe Thr Ile Pro Ser Tyr Met Ile
            180                 185                 190

Ser Tyr Ala Gly Met Val Phe Cys Glu Ala Lys Ile Asn Asp Glu Ser
        195                 200                 205

Tyr Gln Ser Ile Met Tyr Ile Val Val Val Gly Tyr Arg Ile Tyr
    210                 215                 220

Asp Val Val Leu Ser Pro Ser His Gly Ile Glu Leu Ser Val Gly Glu
225                 230                 235                 240

Lys Leu Val Leu Asn Cys Thr Ala Arg Thr Glu Leu Asn Val Gly Ile
                245                 250                 255

Asp Phe Asn Trp Glu Tyr Pro Ser Ser Lys His Gln His Lys Lys Leu
            260                 265                 270

Val Asn Arg Asp Leu Lys Thr Gln Ser Gly Ser Glu Met Lys Lys Phe
        275                 280                 285

Leu Ser Thr Leu Thr Ile Asp Gly Val Thr Arg Ser Asp Gln Gly Leu
    290                 295                 300

Tyr Thr Cys Ala Ala Ser Ser Gly Leu Met Thr Lys Lys Asn Ser Thr
305                 310                 315                 320

Phe Val Arg Val His Glu Lys Pro Phe Val Ala Phe Gly Ser Gly Met
                325                 330                 335

Glu Ser Leu Val Glu Ala Thr Val Gly Glu Arg Val Arg Ile Pro Ala
            340                 345                 350

Lys Tyr Leu Gly Tyr Pro Pro Pro Glu Ile Lys Trp Tyr Lys Asn Gly
        355                 360                 365
```

Ile Pro Leu Glu Ser Asn His Thr Ile Lys Ala Gly His Val Leu Thr
370                 375                 380

Ile Met Glu Val Ser Glu Arg Asp Thr Gly Asn Tyr Thr Val Ile Leu
385                 390                 395                 400

Thr Asn Pro Ile Ser Lys Glu Lys Gln Ser His Val Val Ser Leu Val
                405                 410                 415

Val Tyr Val Pro Pro Gln Ile Gly Glu Lys Ser Leu Ile Ser Pro Val
                420                 425                 430

Asp Ser Tyr Gln Tyr Gly Thr Thr Gln Thr Leu Thr Cys Thr Val Tyr
                435                 440                 445

Ala Ile Pro Pro Pro His His Ile His Trp Tyr Trp Gln Leu Glu Glu
450                 455                 460

Glu Cys Ala Asn Glu Pro Ser His Ala Val Ser Val Thr Asn Pro Tyr
465                 470                 475                 480

Pro Cys Glu Glu Trp Arg Ser Val Glu Asp Phe Gln Gly Gly Asn Lys
                485                 490                 495

Ile Glu Val Asn Lys Asn Gln Phe Ala Leu Ile Glu Gly Lys Asn Lys
                500                 505                 510

Thr Val Ser Thr Leu Val Ile Gln Ala Ala Asn Val Ser Ala Leu Tyr
                515                 520                 525

Lys Cys Glu Ala Val Asn Lys Val Gly Arg Gly Glu Arg Val Ile Ser
530                 535                 540

Phe His Val Thr Arg Gly Pro Glu Ile Thr Leu Gln Pro Asp Met Gln
545                 550                 555                 560

Pro Thr Glu Gln Glu Ser Val Ser Leu Trp Cys Thr Ala Asp Arg Ser
                565                 570                 575

Thr Phe Glu Asn Leu Thr Trp Tyr Lys Leu Gly Pro Gln Pro Leu Pro
                580                 585                 590

Ile His Val Gly Glu Leu Pro Thr Pro Val Cys Lys Asn Leu Asp Thr
                595                 600                 605

Leu Trp Lys Leu Asn Ala Thr Met Phe Ser Asn Ser Thr Asn Asp Ile
610                 615                 620

Leu Ile Met Glu Leu Lys Asn Ala Ser Leu Gln Asp Gln Gly Asp Tyr
625                 630                 635                 640

Val Cys Leu Ala Gln Asp Arg Lys Thr Lys Lys Arg His Cys Val Val
                645                 650                 655

Arg Gln Leu Thr Val Leu Glu Arg Val Ala Pro Thr Ile Thr Gly Asn
                660                 665                 670

Leu Glu Asn Gln Thr Thr Ser Ile Gly Glu Ser Ile Glu Val Ser Cys
                675                 680                 685

Thr Ala Ser Gly Asn Pro Pro Pro Gln Ile Met Trp Phe Lys Asp Asn
690                 695                 700

Glu Thr Leu Val Glu Asp Ser Gly Ile Val Leu Lys Asp Gly Asn Arg
705                 710                 715                 720

Asn Leu Thr Ile Arg Arg Val Arg Lys Glu Asp Glu Gly Leu Tyr Thr
                725                 730                 735

Cys Gln Ala Cys Ser Val Leu Gly Cys Ala Lys Val Glu Ala Phe Phe
                740                 745                 750

Ile Ile Glu Gly Ala Gln Glu Lys Thr Asn Leu Glu
                755                 760

<210> SEQ ID NO 2
<211> LENGTH: 110
<212> TYPE: PRT

<213> ORGANISM: Homo sapiens

<400> SEQUENCE: 2

Pro Glu Ile Thr Leu Gln Pro Asp Met Gln Pro Thr Glu Gln Glu Ser
1               5                   10                  15

Val Ser Leu Trp Cys Thr Ala Asp Arg Ser Thr Phe Glu Asn Leu Thr
            20                  25                  30

Trp Tyr Lys Leu Gly Pro Gln Pro Leu Pro Ile His Val Gly Glu Leu
        35                  40                  45

Pro Thr Pro Val Cys Lys Asn Leu Asp Thr Leu Trp Lys Leu Asn Ala
50                  55                  60

Thr Met Phe Ser Asn Ser Thr Asn Asp Ile Leu Ile Met Glu Leu Lys
65                  70                  75                  80

Asn Ala Ser Leu Gln Asp Gln Gly Asp Tyr Val Cys Leu Ala Gln Asp
                85                  90                  95

Arg Lys Thr Lys Lys Arg His Cys Val Val Arg Gln Leu Thr
            100                 105                 110

<210> SEQ ID NO 3
<211> LENGTH: 87
<212> TYPE: PRT
<213> ORGANISM: Homo sapiens

<400> SEQUENCE: 3

Pro Thr Ile Thr Gly Asn Leu Glu Asn Gln Thr Thr Ser Ile Gly Glu
1               5                   10                  15

Ser Ile Glu Val Ser Cys Thr Ala Ser Gly Asn Pro Pro Pro Gln Ile
            20                  25                  30

Met Trp Phe Lys Asp Asn Glu Thr Leu Val Glu Asp Ser Gly Ile Val
        35                  40                  45

Leu Lys Asp Gly Asn Arg Asn Leu Thr Ile Arg Arg Val Arg Lys Glu
50                  55                  60

Asp Glu Gly Leu Tyr Thr Cys Gln Ala Cys Ser Val Leu Gly Cys Ala
65                  70                  75                  80

Lys Val Glu Ala Phe Phe Ile
                85

<210> SEQ ID NO 4
<211> LENGTH: 10
<212> TYPE: PRT
<213> ORGANISM: Mus musculus

<400> SEQUENCE: 4

Gly Tyr Ala Phe Thr Thr Tyr Trp Met His
1               5                   10

<210> SEQ ID NO 5
<211> LENGTH: 17
<212> TYPE: PRT
<213> ORGANISM: Mus musculus

<400> SEQUENCE: 5

Met Ile Asp Phe Ser Asp Ser Glu Thr Lys Leu Asn Gln Arg Phe Lys
1               5                   10                  15

Gly

<210> SEQ ID NO 6
<211> LENGTH: 8
<212> TYPE: PRT

<213> ORGANISM: Mus musculus

<400> SEQUENCE: 6

Asp Val Arg Gly Asn Phe Asp Val
1               5

<210> SEQ ID NO 7
<211> LENGTH: 15
<212> TYPE: PRT
<213> ORGANISM: Mus musculus

<400> SEQUENCE: 7

Arg Ala Ser Lys Ser Val Ser Thr Ser Gly Tyr Ser Tyr Met His
1               5                   10                  15

<210> SEQ ID NO 8
<211> LENGTH: 7
<212> TYPE: PRT
<213> ORGANISM: Mus musculus

<400> SEQUENCE: 8

Leu Ala Ser Asn Leu Glu Ser
1               5

<210> SEQ ID NO 9
<211> LENGTH: 9
<212> TYPE: PRT
<213> ORGANISM: Mus musculus

<400> SEQUENCE: 9

Gln His Ser Arg Glu Leu Pro Trp Thr
1               5

<210> SEQ ID NO 10
<211> LENGTH: 10
<212> TYPE: PRT
<213> ORGANISM: Mus musculus

<400> SEQUENCE: 10

Gly Tyr Ser Phe Thr Asp Tyr Ser Met Tyr
1               5                   10

<210> SEQ ID NO 11
<211> LENGTH: 17
<212> TYPE: PRT
<213> ORGANISM: Mus musculus

<400> SEQUENCE: 11

Tyr Ile Asp Pro Tyr Asn Asp Asp Thr Ser Tyr Lys Gln Lys Phe Lys
1               5                   10                  15

Gly

<210> SEQ ID NO 12
<211> LENGTH: 8
<212> TYPE: PRT
<213> ORGANISM: Mus musculus

<400> SEQUENCE: 12

Gly Tyr Ala Asp Ala Met Asp Tyr
1               5

<210> SEQ ID NO 13
<211> LENGTH: 11
<212> TYPE: PRT

<210> SEQ ID NO 13
<211> LENGTH: 11
<212> TYPE: PRT
<213> ORGANISM: Mus musculus

<400> SEQUENCE: 13

His Ala Ser Gln Asn Ile Asn Val Trp Leu Ser
1               5                   10

<210> SEQ ID NO 14
<211> LENGTH: 7
<212> TYPE: PRT
<213> ORGANISM: Mus musculus

<400> SEQUENCE: 14

Lys Ala Ser Asn Leu His Thr
1               5

<210> SEQ ID NO 15
<211> LENGTH: 9
<212> TYPE: PRT
<213> ORGANISM: Mus musculus

<400> SEQUENCE: 15

Gln Gln Gly Gln Ser Tyr Pro Leu Thr
1               5

<210> SEQ ID NO 16
<211> LENGTH: 351
<212> TYPE: DNA
<213> ORGANISM: Mus musculus
<220> FEATURE:
<221> NAME/KEY: CDS
<222> LOCATION: (1)..(351)

<400> SEQUENCE: 16

```
gag gtg cag ctg cag cag tct ggg cct cag ctg gtt agg cct ggg gct      48
Glu Val Gln Leu Gln Gln Ser Gly Pro Gln Leu Val Arg Pro Gly Ala
1               5                   10                  15 tca gcg aag ata tcc tgc aag gct tct ggt tac gca ttc acc acc tac      96
Ser Ala Lys Ile Ser Cys Lys Ala Ser Gly Tyr Ala Phe Thr Thr Tyr
            20                  25                  30 tgg atg cac tgg gtg aaa cag agg cct gga caa ggt ctt gag tgg att     144
Trp Met His Trp Val Lys Gln Arg Pro Gly Gln Gly Leu Glu Trp Ile
        35                  40                  45 ggc atg att gat ttt tcc gat agt gaa act aag tta aat cag agg ttc     192
Gly Met Ile Asp Phe Ser Asp Ser Glu Thr Lys Leu Asn Gln Arg Phe
    50                  55                  60 aag ggc aag gcc aca ttg act gtt gac aaa tcc tcc agc aca gcc tac     240
Lys Gly Lys Ala Thr Leu Thr Val Asp Lys Ser Ser Ser Thr Ala Tyr
65                  70                  75                  80 atg caa ctc agc agc ccg aca tct gag gac tct gcg gtc tat tac tgt     288
Met Gln Leu Ser Ser Pro Thr Ser Glu Asp Ser Ala Val Tyr Tyr Cys
                85                  90                  95 gca aga gat gtc aga ggg aac ttc gat gtc tgg ggc gca ggg acc acg     336
Ala Arg Asp Val Arg Gly Asn Phe Asp Val Trp Gly Ala Gly Thr Thr
            100                 105                 110 gtc acc gtc tcc tca                                                  351
Val Thr Val Ser Ser
        115
```

<210> SEQ ID NO 17
<211> LENGTH: 117
<212> TYPE: PRT
<213> ORGANISM: Mus musculus

<400> SEQUENCE: 17

```
Glu Val Gln Leu Gln Gln Ser Gly Pro Gln Leu Val Arg Pro Gly Ala
1               5                   10                  15

Ser Ala Lys Ile Ser Cys Lys Ala Ser Gly Tyr Ala Phe Thr Thr Tyr
            20                  25                  30

Trp Met His Trp Val Lys Gln Arg Pro Gly Gln Gly Leu Glu Trp Ile
        35                  40                  45

Gly Met Ile Asp Phe Ser Asp Ser Glu Thr Lys Leu Asn Gln Arg Phe
    50                  55                  60

Lys Gly Lys Ala Thr Leu Thr Val Asp Lys Ser Ser Thr Ala Tyr
65                  70                  75                  80

Met Gln Leu Ser Ser Pro Thr Ser Glu Asp Ser Ala Val Tyr Tyr Cys
            85                  90                  95

Ala Arg Asp Val Arg Gly Asn Phe Asp Val Trp Gly Ala Gly Thr Thr
            100                 105                 110

Val Thr Val Ser Ser
        115
```

<210> SEQ ID NO 18
<211> LENGTH: 336
<212> TYPE: DNA
<213> ORGANISM: Mus musculus
<220> FEATURE:
<221> NAME/KEY: CDS
<222> LOCATION: (1)..(336)

<400> SEQUENCE: 18

```
gat att gtg ttg aca cag tct cct gct tcc tta gct gta tct ctg ggg     48
Asp Ile Val Leu Thr Gln Ser Pro Ala Ser Leu Ala Val Ser Leu Gly
1               5                   10                  15 cag agg gcc acc atc tca tgc agg gcc agc aaa agt gtc agt aca tct    96
Gln Arg Ala Thr Ile Ser Cys Arg Ala Ser Lys Ser Val Ser Thr Ser
            20                  25                  30 ggc tat agt tat atg cac tgg tac caa cag aaa cca gga cag cca ccc   144
Gly Tyr Ser Tyr Met His Trp Tyr Gln Gln Lys Pro Gly Gln Pro Pro
        35                  40                  45 aaa ctc ctc atc tat ctt gca tcc aac cta gaa tct ggg gtc cct gcc   192
Lys Leu Leu Ile Tyr Leu Ala Ser Asn Leu Glu Ser Gly Val Pro Ala
    50                  55                  60 agg ttc agt ggc agt ggg tct ggg aca gac ttc acc ctc aac atc cat   240
Arg Phe Ser Gly Ser Gly Ser Gly Thr Asp Phe Thr Leu Asn Ile His
65                  70                  75                  80 cct gtg gag gag gag gat gct gca acc tat tac tgt cag cac agt agg   288
Pro Val Glu Glu Glu Asp Ala Ala Thr Tyr Tyr Cys Gln His Ser Arg
            85                  90                  95 gag ctt ccg tgg acg ttc ggt gga ggc acc aag ctg gaa atc aaa cgt   336
Glu Leu Pro Trp Thr Phe Gly Gly Gly Thr Lys Leu Glu Ile Lys Arg
            100                 105                 110
```

<210> SEQ ID NO 19
<211> LENGTH: 112
<212> TYPE: PRT
<213> ORGANISM: Mus musculus

<400> SEQUENCE: 19

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Met His Trp Tyr Gln Gln Lys Pro Gly Gln Pro Pro
```

```
                35                  40                  45
Lys Leu Leu Ile Tyr Leu Ala Ser Asn Leu Glu Ser Gly Val Pro Ala
        50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Trp Thr Phe Gly Gly Gly Thr Lys Leu Glu Ile Lys Arg
            100                 105                 110

<210> SEQ ID NO 20
<211> LENGTH: 351
<212> TYPE: DNA
<213> ORGANISM: Mus musculus
<220> FEATURE:
<221> NAME/KEY: CDS
<222> LOCATION: (1)..(351)

<400> SEQUENCE: 20 cag gtc cag ctg cag cag tct gga cct gaa ctg gtg aag cct ggg gct      48
Gln Val Gln Leu Gln Gln Ser Gly Pro Glu Leu Val Lys Pro Gly Ala
1               5                   10                  15 tca gtg aag gta tcc tgc aag gct tct ggt tac tca ttc act gac tac      96
Ser Val Lys Val Ser Cys Lys Ala Ser Gly Tyr Ser Phe Thr Asp Tyr
            20                  25                  30 agc atg tac tgg gtg aag cag agc cat gga aag agc ctt gag tgg att     144
Ser Met Tyr Trp Val Lys Gln Ser His Gly Lys Ser Leu Glu Trp Ile
        35                  40                  45 gga tat att gat cct tac aat gat gat act agc tac aag cag aag ttc     192
Gly Tyr Ile Asp Pro Tyr Asn Asp Asp Thr Ser Tyr Lys Gln Lys Phe
    50                  55                  60 aag ggc aag gcc aca ttg act gtt gac aag tcc tcc agc aca gcc ttc     240
Lys Gly Lys Ala Thr Leu Thr Val Asp Lys Ser Ser Ser Thr Ala Phe
65                  70                  75                  80 atg cat ctc aac agc ctg aca tct gag gac tct gca gtc tat tac tgt     288
Met His Leu Asn Ser Leu Thr Ser Glu Asp Ser Ala Val Tyr Tyr Cys
                85                  90                  95 gca aag ggt tac gcg gat gct atg gac tac tgg ggt caa gga acc tca     336
Ala Lys Gly Tyr Ala Asp Ala Met Asp Tyr Trp Gly Gln Gly Thr Ser
            100                 105                 110 gtc acc gtc tcc tca                                                  351
Val Thr Val Ser Ser
        115

<210> SEQ ID NO 21
<211> LENGTH: 117
<212> TYPE: PRT
<213> ORGANISM: Mus musculus

<400> SEQUENCE: 21

Gln Val Gln Leu Gln Gln Ser Gly Pro Glu Leu Val Lys Pro Gly Ala
1               5                   10                  15

Ser Val Lys Val Ser Cys Lys Ala Ser Gly Tyr Ser Phe Thr Asp Tyr
            20                  25                  30

Ser Met Tyr Trp Val Lys Gln Ser His Gly Lys Ser Leu Glu Trp Ile
        35                  40                  45

Gly Tyr Ile Asp Pro Tyr Asn Asp Asp Thr Ser Tyr Lys Gln Lys Phe
    50                  55                  60

Lys Gly Lys Ala Thr Leu Thr Val Asp Lys Ser Ser Ser Thr Ala Phe
65                  70                  75                  80
```

```
Met His Leu Asn Ser Leu Thr Ser Glu Asp Ser Ala Val Tyr Tyr Cys
                85                  90                  95

Ala Lys Gly Tyr Ala Asp Ala Met Asp Tyr Trp Gly Gln Gly Thr Ser
            100                 105                 110

Val Thr Val Ser Ser
        115

<210> SEQ ID NO 22
<211> LENGTH: 324
<212> TYPE: DNA
<213> ORGANISM: Mus musculus
<220> FEATURE:
<221> NAME/KEY: CDS
<222> LOCATION: (1)..(324)

<400> SEQUENCE: 22 gat att cag atg att cag tct cca tcc agt ctg tct gca tcc ctt gga     48
Asp Ile Gln Met Ile Gln Ser Pro Ser Ser Leu Ser Ala Ser Leu Gly
1               5                   10                  15 gac aca att acc atc act tgc cat gcc agt cag aac att aat gtt tgg     96
Asp Thr Ile Thr Ile Thr Cys His Ala Ser Gln Asn Ile Asn Val Trp
            20                  25                  30 tta agc tgg tac cag cag aaa cca gga aat att cct aaa cta ttg atc    144
Leu Ser Trp Tyr Gln Gln Lys Pro Gly Asn Ile Pro Lys Leu Leu Ile
        35                  40                  45 tat aag gct tcc aac ttg cac aca ggc gtc cca tca agg ttt agt ggc    192
Tyr Lys Ala Ser Asn Leu His Thr Gly Val Pro Ser Arg Phe Ser Gly
    50                  55                  60 agt gga tct gga aca ggt ttc aca tta acc atc agc agc ctg cag cct    240
Ser Gly Ser Gly Thr Gly Phe Thr Leu Thr Ile Ser Ser Leu Gln Pro
65                  70                  75                  80 gaa gac att gcc acc tac tac tgt caa cag ggt caa agt tat ccg ctc    288
Glu Asp Ile Ala Thr Tyr Tyr Cys Gln Gln Gly Gln Ser Tyr Pro Leu
                85                  90                  95 acg ttc ggt gct ggg acc aag ctg gag ctg aaa cgg                    324
Thr Phe Gly Ala Gly Thr Lys Leu Glu Leu Lys Arg
            100                 105

<210> SEQ ID NO 23
<211> LENGTH: 108
<212> TYPE: PRT
<213> ORGANISM: Mus musculus

<400> SEQUENCE: 23

Asp Ile Gln Met Ile Gln Ser Pro Ser Ser Leu Ser Ala Ser Leu Gly
1               5                   10                  15

Asp Thr Ile Thr Ile Thr Cys His Ala Ser Gln Asn Ile Asn Val Trp
            20                  25                  30

Leu Ser Trp Tyr Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Gly Gln Ser Tyr Pro Leu
                85                  90                  95

Thr Phe Gly Ala Gly Thr Lys Leu Glu Leu Lys Arg
            100                 105
```

```
<210> SEQ ID NO 24
<211> LENGTH: 351
<212> TYPE: DNA
<213> ORGANISM: artificial
<220> FEATURE:
<223> OTHER INFORMATION: humanized antibody
<220> FEATURE:
<221> NAME/KEY: CDS
<222> LOCATION: (1)..(351)

<400> SEQUENCE: 24 caa gtg cag ctg gtg cag tct ggc gcc gaa gtg aag aaa cca ggc gcc        48
Gln Val Gln Leu Val Gln Ser Gly Ala Glu Val Lys Lys Pro Gly Ala
1               5                   10                  15 agc gtg aag gtg tcc tgc aag gcc agc ggc tac gcc ttc acc acc tac        96
Ser Val Lys Val Ser Cys Lys Ala Ser Gly Tyr Ala Phe Thr Thr Tyr
            20                  25                  30 tgg atg cat tgg gtg cgc cag gcc cct gga cag ggc ctg gaa tgg atc       144
Trp Met His Trp Val Arg Gln Ala Pro Gly Gln Gly Leu Glu Trp Ile
        35                  40                  45 ggc atg atc gac ttc agc gac agc gag aca aag ctg aac cag cgg ttc       192
Gly Met Ile Asp Phe Ser Asp Ser Glu Thr Lys Leu Asn Gln Arg Phe
    50                  55                  60 aag ggc aag gcc acc ctg acc gtg gac aag agc acc agc acc gcc tac       240
Lys Gly Lys Ala Thr Leu Thr Val Asp Lys Ser Thr Ser Thr Ala Tyr
65                  70                  75                  80 atg gaa ctg agc agc ctg cgg agc gag gac acc gcc gtg tac tac tgc       288
Met Glu Leu Ser Ser Leu Arg Ser Glu Asp Thr Ala Val Tyr Tyr Cys
                85                  90                  95 gct aga gat gtg cgg ggc aac ttc gac gtg tgg ggc cag gga aca ctc       336
Ala Arg Asp Val Arg Gly Asn Phe Asp Val Trp Gly Gln Gly Thr Leu
            100                 105                 110 gtg acc gtg tct agc                                                   351
Val Thr Val Ser Ser
        115

<210> SEQ ID NO 25
<211> LENGTH: 117
<212> TYPE: PRT
<213> ORGANISM: artificial
<220> FEATURE:
<223> OTHER INFORMATION: Synthetic Construct

<400> SEQUENCE: 25

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Thr Tyr
            20                  25                  30

Trp Met His Trp Val Arg Gln Ala Pro Gly Gln Gly Leu Glu Trp Ile
        35                  40                  45

Gly Met Ile Asp Phe Ser Asp Ser Glu Thr Lys Leu Asn Gln Arg Phe
    50                  55                  60

Lys Gly Lys Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Val Arg Gly Asn Phe Asp Val Trp Gly Gln Gly Thr Leu
            100                 105                 110

Val Thr Val Ser Ser
        115
```

<210> SEQ ID NO 26
<211> LENGTH: 336
<212> TYPE: DNA
<213> ORGANISM: Artificial Sequence
<220> FEATURE:
<223> OTHER INFORMATION: Humanized antibody
<220> FEATURE:
<221> NAME/KEY: CDS
<222> LOCATION: (1)..(336)

<400> SEQUENCE: 26

```
gac atc cag atg acc cag agc ccc agc agc ctg tct gcc agc gtg ggc      48
Asp Ile Gln Met Thr Gln Ser Pro Ser Ser Leu Ser Ala Ser Val Gly
1               5                   10                  15 gac aga gtg acc atc acc tgt cgg gcc agc aag agc gtg tcc acc agc      96
Asp Arg Val Thr Ile Thr Cys Arg Ala Ser Lys Ser Val Ser Thr Ser
            20                  25                  30 ggc tac agc tac atg cac tgg tat cag cag aag ccc ggc aag gcc ccc     144
Gly Tyr Ser Tyr Met His Trp Tyr Gln Gln Lys Pro Gly Lys Ala Pro
        35                  40                  45 aag ctg ctg atc tac ctg gcc agc aac ctg gaa agc ggc gtg ccc agc     192
Lys Leu Leu Ile Tyr Leu Ala Ser Asn Leu Glu Ser Gly Val Pro Ser
50                  55                  60 aga ttt tcc ggc agc ggc tct ggc acc gac ttc acc ctg acc atc agc     240
Arg Phe Ser Gly Ser Gly Ser Gly Thr Asp Phe Thr Leu Thr Ile Ser
65                  70                  75                  80 tcc ctg cag ccc gag gac ttc gcc acc tac tac tgc cag cac agc aga     288
Ser Leu Gln Pro Glu Asp Phe Ala Thr Tyr Tyr Cys Gln His Ser Arg
                85                  90                  95 gag ctg ccc tgg acc ttt ggc cag ggc acc aag gtg gaa atc aag cgg     336
Glu Leu Pro Trp Thr Phe Gly Gln Gly Thr Lys Val Glu Ile Lys Arg
            100                 105                 110
```

<210> SEQ ID NO 27
<211> LENGTH: 112
<212> TYPE: PRT
<213> ORGANISM: Artificial Sequence
<220> FEATURE:
<223> OTHER INFORMATION: Synthetic Construct

<400> SEQUENCE: 27

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Val Ser Thr Ser
            20                  25                  30

Gly Tyr Ser Tyr Met His Trp Tyr Gln Gln Lys Pro Gly Lys Ala Pro
        35                  40                  45

Lys Leu Leu Ile Tyr Leu Ala Ser Asn Leu Glu Ser Gly Val Pro Ser
50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Arg
                85                  90                  95

Glu Leu Pro Trp Thr Phe Gly Gln Gly Thr Lys Val Glu Ile Lys Arg
            100                 105                 110
```

ANTI-VEGFR ANTIBODY AND USES THEREOF

RELATED APPLICATION

This application is a continuation of application Ser. No. 15/393,534 filed Dec. 29, 2016 which claims the benefit of U.S. Provisional Application 62/273,515 filed Dec. 31, 2015, the entire contents of which are incorporated herein by reference.

FIELD OF THE INVENTION

The present invention relates to an antibody or antigen-binding fragment thereof, which is specific to human vascular endothelial growth factor receptor (VEGFR), and uses thereof.

BACKGROUND OF THE INVENTION

The function of signal transduction pathway by vascular endothelial growth factor (VEGF) is promoting angiogenesis. Angiogenesis means the formation of new capillaries from original blood vessels. Abnormalities of angiogenesis regulation relate to pathogenic mechanisms of many diseases, and are also a feature of many types of cancer. The main roles participating in the signal transduction pathway are proteins belonging to a vascular endothelial growth factor family and receptors thereof. Activation of this signal transduction pathway activates complex networks downstream, and promotes the growth, migration and survival of vascular endothelial cells. This signaling transduction pathway is regarded as being closely connected to tumor angiogenesis, so the inhibition of signal transduction pathway is important for the regulation of tumor angiogenesis.

The vascular endothelial growth factor family comprises a group of homologous dimeric glycoproteins having highly conserved sequences. The members in the vascular endothelial growth factor family are activated by linking two 24 kDa single-stranded molecules through a disulfide bond. The known members in the vascular endothelial growth factor family include VEGF-A, VEGF-B, VEGF-C, VEGF-D, and placenta growth factor (PlGF), and wherein VEGF-A is first found and studied most thoroughly, which plays a critical role in angiogenesis.

When the vascular endothelial growth factor binds to vascular endothelial growth factor receptors (VEGF receptor, VEGFR), the vascular endothelial growth factor receptors form a dimer and phosphorylate each other. There are seven Ig-like domains located in the extracellular region of the vascular endothelial growth factor receptor. Generally, domains 1 to 3 are responsible for binding with the ligands, and domains 4 to 7 are responsible for dimerization, phosphorylation and downstream signal transduction.

The vascular endothelial growth factor receptor belongs to the tyrosine kinase (TK) family and is a key member in the signal transduction pathway. It transducts the extracellular signals of inducing cell growth, proliferation and anti-apoptosis into the cell. There are three types of the vascular endothelial growth factor receptor: VEGFR-1 (also known as flt-1), VEGFR-2 (also known as KDR/flk-1) and VEGFR-3 (also known as flt-4). VEGF-A binds to VEGFR-1 and VEGFR-2, and these two receptors are both expressed in the vascular endothelial cells, and the signals of the vascular endothelial cell are mainly transducted through VEGFR-2. Although the binding affinity between VEGFR-1 and the ligands is 10-folds stronger than that between VEGFR-2 and the ligands, the kinase activity of VEGFR-1 is weaker. In another aspect, VEGFR-3 is mainly expressed in lymphatic endothelial cells.

In addition to being by original peripheral vascular endothelial cell proliferation, it is also known that the tumor angiogenesis is formed by attracting vascular endothelial progenitor cells to move to the tumor or peripheral regions thereof under the regulation of VEGFR-2, and then the vascular endothelial progenitor cells are differentiated into the vascular endothelial cells. Because the angiogenesis relating to vascular endothelial growth factor receptor occurs only in wound repair and menstrual cycles of women in a normal physiological condition, the influence of blocking the signal transduction pathway by vascular endothelial growth factor receptor is limited to the normal physiological function. As a result, inhibiting signal transduction pathway by vascular endothelial growth factor receptor becomes an important regulatory point of inhibition of tumor angiogenesis and leading to tumor cell death consequently. It had been reported that vascular endothelial growth factors are over-expressed in a variety of solid tumors, such as colorectal cancer, breast cancer, prostate cancer, and lung cancer.

Thus, there is need for developing a novel approach to block signal transduction pathway by vascular endothelial growth factor receptor.

SUMMARY OF THE INVENTION

The present invention provides an antibody or antigen-binding fragment thereof that binds human vascular endothelial growth factor receptor 2 or a human vascular endothelial growth factor receptor 2 fragment. The antibody according to the invention are useful for inhibiting VEGFR-2-mediated signaling and for treating diseases and disorders caused by or related to VEGFR-2 activity and/or signaling. The antibody of the invention is also useful for inhibiting cell proliferation of endothelial cells.

The present invention provides a method for inhibiting VEGFR-2-mediated signaling in a subject in need, comprising administering to the subject a pharmaceutical composition comprising the antibody or antigen-binding fragment thereof as mentioned above.

The present invention provides a method for treating diseases and/or disorders caused by or related to VEGFR-2 activity and/or signaling in a subject afflicted with the diseases and/or disorders, comprising administering to the subject a pharmaceutical composition comprising the antibody or antigen-binding fragment thereof as mentioned above.

The present invention provides a method for treating tumor in a subject afflicted with the tumor, comprising administering to the subject a pharmaceutical composition comprising the antibody or antigen-binding fragment thereof as mentioned above.

The present invention provides a method for inhibiting cell proliferation of endothelial cells in a subject in need, comprising administering to the subject a pharmaceutical composition comprising the antibody or antigen-binding fragment thereof as mentioned above.

The present invention provides a method for detecting human vascular endothelial growth factor receptor in a sample comprising contacting the sample with the antibody or antigen-binding fragment thereof as mentioned above.

The present invention is described in detail in the following sections. Other characteristics, purposes and advantages of the present invention can be found in the detailed description and claims.

BRIEF DESCRIPTION OF THE DRAWINGS

FIG. 1 shows the ELISA result of binding affinity assay of the antibodies of the invention to mouse VEGFR-2, human VEGFR-1 or VEGFR-3.

FIG. 2 shows the ELISA result of binding domain mapping (domains 1 to 3 and domains 4 to 7) of the antibodies of the invention.

FIG. 8 shows the result of size-exclusion chromatography analysis of the antibody-drug conjugate (ADC) according to the invention.

FIG. 12 shows quantification assay of the chimeric antigen receptor T cell (CAR-T) according to the invention by flow cytometry.

FIG. 13 shows cytotoxicity assay of the chimeric antigen receptor T cell according to the invention.

FIG. 14 shows the efficiency of the labeling the antibodies according to the invention with radioisotope.

FIG. 16 shows the alignment of $V_L$ segments of the humanized, mouse, and human antibodies. M: 322A6; Hd: Hu322B1HdH.

FIG. 17 shows the alignment of $V_H$ segments of the humanized, mouse, and human antibodies. M: 322A6; Hu: human template IGHV1-46*01 F; HuB1: Hu322B1HdH.

DETAILED DESCRIPTION OF THE INVENTION

Figure 3A:
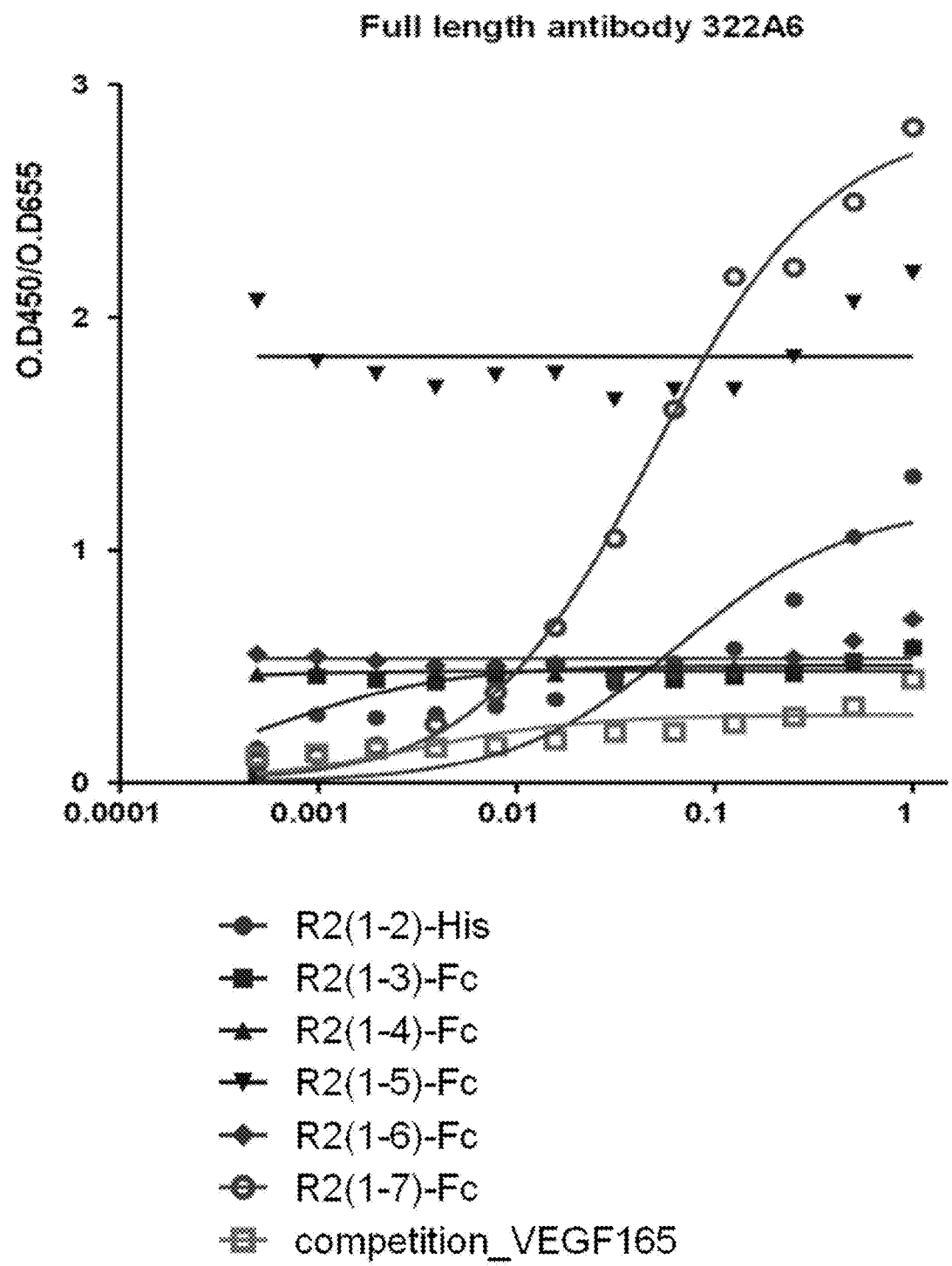
FIG. 3A, FIG. 3B and FIG. 3C show the ELISA result of binding domain mapping of the antibodies of the invention.

The present invention provides an antibody or antigen-binding fragment thereof that binds to human vascular endothelial growth factor receptor 2 or a human vascular endothelial growth factor receptor 2 fragment.

Particularly, the antibody or antigen-binding fragment thereof according to the invention specifically binds to an epitope in human vascular endothelial growth factor receptor 2 or a fragment thereof; wherein the human vascular endothelial growth factor receptor 2 has the amino acid sequence of SEQ ID NO: 1, and the epitope comprises:
the leucine residue at position 606, the aspartic acid residue at position 607, the arginine residue at position 647, the lysine residue at position 648, and the threonine residue at position 649 of SEQ ID NO: 1; or
the serine residue at position 711, the lysine residue at position 716, the aspartic acid residue at position 717, and the arginine residues at positions 725 and 726 of SEQ ID NO: 1.

The antibody according to the invention can be full-length (for example, an IgG1 or IgG4 antibody) or may comprise only an antigen-binding portion (for example, a Fab, F(ab')$_2$ or scFv fragment), and may be modified to affect functionality as needed.

The antibody or antigen-binding fragment thereof according to the invention specifically binds to human VEGFR-2. VEGFR-2, also known as KDR or flk-1, is a receptor of vascular endothelial growth factor, and is activated by forming a dimer and phosphorylating each other of the dimer when binds to the ligands thereof. VEGFR-2 comprises seven Ig-like domains located in the extracellular region, and wherein domains 1 to 3 are responsible for binding with the ligands, and domains 4 to 7 are responsible for dimerization, phosphorylation and downstream signal transduction. Preferably, the antibody or antigen-binding fragment thereof according to the invention binds to domains 6 to 7 of the extracellular region of VEGFR-2.

The present invention includes an anti-VEGFR-2 antibody and antigen-binding fragment thereof that binds monomeric or dimeric VEGFR-2 molecules with high affinity.

In one preferred embodiment of the invention, VEGFR-2 has the amino acid sequence of SEQ ID NO: 1; the domain 6 of the extracellular region of VEGFR-2 has the amino acid sequence of SEQ ID NO: 2; and the domain 7 of the extracellular region of VEGFR-2 has the amino acid sequence of SEQ ID NO: 3.

Various techniques known to persons of ordinary skill in the art can be used to determine whether an antibody "specifically binds to one or more amino acids" within a polypeptide or protein. Exemplary techniques include, e.g., routine cross-blocking assay such as that described Antibodies, Harlow and Lane (Cold Spring Harbor Press, Cold Spring Harb., N.Y.), alanine scanning mutational analysis, peptide blots analysis (Reineke, 2004, Methods Mol Biol 248:443-463), and peptide cleavage analysis. In addition, methods such as epitope excision, epitope extraction and chemical modification of antigens can be employed (Tomer, 2000, Protein Science 9:487-496). Another method that can be used to identify the amino acids within a polypeptide with which an antibody specifically binds is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water to allow hydrogen-deuterium exchange to occur at all residues except for the residues protected by the antibody (which remain deuterium-labeled). After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) Analytical Biochemistry 267(2):252-259; Engen and Smith (2001) Anal. Chem. 73:256A-265A.

In one preferred embodiment of the invention, the epitope of VEGFR-2 comprises the leucine residue at position 606, the aspartic acid residue at position 607, the arginine residue at position 647, the lysine residue at position 648, and the threonine residue at position 649 of SEQ ID NO: 1.

In one another preferred embodiment of the invention, the epitope of VEGFR-2 comprises the serine residue at position 711, the lysine residue at position 716, the aspartic acid residue at position 717, and the arginine residues at positions 725 and 726 of SEQ ID NO: 1.

The present invention further includes an anti-VEGFR antibody that specifically binds to the same epitope. Likewise, the present invention also includes an anti-VEGFR-2 antibody that competes for binding to VEGFR-2 with any of the specific exemplary antibodies described herein.

One can easily determine whether an antibody specifically binds to the same epitope as, or competes for binding with, a reference anti-VEGFR-2 antibody by using routine methods known in the art. For example, to determine if a test antibody binds to the same epitope as a reference anti-VEGFR-2 antibody of the invention, the reference antibody is allowed to bind to an VEGFR-2 protein (e.g., a soluble portion of the VEGFR-2 extracellular domain or cell surface-expressed VEGFR-2). Next, the ability of a test antibody to bind to the VEGFR-2 molecule is assessed. If the test antibody is able to bind to VEGFR-2 following saturation binding with the reference anti-VEGFR-2 antibody, it can be concluded that the test antibody binds to a different epitope than the reference anti-VEGFR-2 antibody. On the other hand, if the test antibody is not able to bind to the VEGFR-2 molecule following saturation binding with the reference anti-VEGFR-2 antibody, then the test antibody may bind to the same epitope as the epitope bound by the reference anti-VEGFR-2 antibody of the invention. Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, Biacore, flow cytometry or any other quantitative or qualitative antibody-binding assay available in the art. In accordance with certain embodiments of the present invention, two antibodies bind to the same (or overlapping) epitope if, e.g., a 1-, 5-, 10-, 20- or 100-fold excess of one antibody inhibits binding of the other by at least 50% but preferably 75%, 90% or even 99% as measured in a competitive binding assay. Alternatively, two antibodies are deemed to bind to the same epitope if essentially all amino acid mutations in the antigen that reduce or eliminate binding of one antibody reduce or eliminate binding of the other. Two antibodies are deemed to have "overlapping epitopes" if only a subset of the amino acid mutations that reduce or eliminate binding of one antibody reduce or eliminate binding of the other.

To determine if an antibody competes for binding with a reference anti-VEGFR-2 antibody, the above-described binding methodology is performed in two orientations: In a first orientation, the reference antibody is allowed to bind to an VEGFR-2 protein (e.g., a soluble portion of the VEGFR-2 extracellular domain or cell surface-expressed VEGFR-2) under saturating conditions followed by assessment of binding of the test antibody to the VEGFR-2 molecule. In a second orientation, the test antibody is allowed to bind to a VEGFR-2 molecule under saturating conditions followed by assessment of binding of the reference antibody to the VEGFR-2 molecule. If, in both orientations, only the first (saturating) antibody is capable of binding to the VEGFR-2 molecule, then it is concluded that the test antibody and the reference antibody compete for binding to VEGFR-2. As will be appreciated by a person of ordinary skill in the art, an antibody that competes for binding with a reference antibody may not necessarily bind to the same epitope as the reference antibody, but may sterically block binding of the reference antibody by binding an overlapping or adjacent epitope.

The term "antibody", as used herein, means any antigen-binding molecule or molecular complex comprising at least one complementarity determining region (CDR) that specifically binds to or interacts with a particular antigen (e.g., VEGFR-2). The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_{H1}$, $C_{H2}$ and $C_{H3}$. Each light chain comprises a light chain variable region (abbreviated herein as LCVR or $V_L$) and a light chain constant region. The light chain constant region comprises one domain ($C_{L1}$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-VEGFR antibody (or antigen-binding portion thereof) may be identical to the human germline sequences, or may be naturally or artificially modified. An amino acid consensus sequence may be defined based on a side-by-side analysis of two or more CDRs.

The term "antibody", as used herein, also includes an antigen-binding fragment of a full antibody molecule. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. An antigen-binding fragment of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of an antigen-binding fragment includes: (i) Fab fragments; (ii) F(ab')$_2$ fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody typically comprises at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_{H1}$; (ii) $V_H$-$C_{H2}$; (iii) $V_H$-$C_{H3}$; (iv) $V_H$-$C_{H1}$-$C_{H2}$; (V) $V_H$-$C_{H1}$-$C_{H2}$-$C_{H3}$; (vi) $V_H$-$C_{H2}$-$C_{H3}$; (vii) $V_H$-$C_L$; (viii) $V_L$-$C_{H1}$; (ix) $V_L$-$C_{H2}$; (x) $V_L$-$C_{H3}$; (xi) $V_L$-$C_{H1}$-$C_{H2}$; (xii) $V_L$-$C_{H1}$-$C_{H2}$-$C_{H3}$; (xiii) $V_L$-$C_{H2}$-$C_{H3}$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with a full antibody molecule, an antigen-binding fragment may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

Preferably, the antibody or antigen-binding fragment thereof according to the invention is a mammalian antibody.

The term "mammalian antibody", as used herein, is intended to include antibodies having variable and constant regions derived from mammalian germline immunoglobulin sequences. The mammalian antibodies of the invention may include amino acid residues not encoded by mammalian germline immunoglobulin sequences (e.g., mutations introduced by random or site-specific mutagenesis in vitro or by somatic mutation in vivo), for example in the CDRs and in particular CDR3.

The term "recombinant mammalian antibody", as used herein, is intended to include all mammalian antibodies that are prepared, expressed, created or isolated by recombinant means, such as antibodies expressed using a recombinant expression vector transfected into a host cell (described further below), antibodies isolated from a recombinant, combinatorial mammalian antibody library (described further below), antibodies isolated from an animal (e.g., a mouse) that is transgenic for mammalian immunoglobulin genes or antibodies prepared, expressed, created or isolated by any other means that involves splicing of mammalian immunoglobulin gene sequences to other DNA sequences. Such recombinant mammalian antibodies have variable and constant regions derived from mammalian germline immunoglobulin sequences. In certain embodiments, however, such recombinant mammalian antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the mammalian antibody germline repertoire in vivo.

Mammalian antibodies such as human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The anti-VEGFR-2 antibody disclosed herein may comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present invention includes an antibody, and an antigen-binding fragment thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another mammalian germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes an anti-VEGFR-2 antibody comprising variants of any of the $V_H$, $V_L$, and/or CDR amino acid sequences disclosed herein having one or more conservative substitutions. For example, the present invention includes an anti-VEGFR-2 antibody having $V_H$, $V_L$, and/or CDR amino acid sequences with, e.g., 10 or fewer, 8 or fewer, 6 or fewer, 4 or fewer, etc. conservative amino acid substitutions relative to any of the $V_H$, $V_L$, and/or CDR amino acid sequences disclosed herein.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445, herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutant thereof. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402, each herein incorporated by reference.

In one preferred embodiment of the invention, the antibody or antigen-binding fragment thereof comprises complementarity determining regions of a heavy chain variable region and complementarity determining regions of a light chain variable region, wherein the complementarity determining regions of the heavy chain variable region comprises CDRH1, CDRH2 and CDRH3 regions, and the complementarity determining regions of the light chain variable region comprises CDRL1, CDRL2 and CDRL3 regions, and the CDRH1 region comprises the amino acid sequence of SEQ ID NO: 4, or a substantially similar sequence thereof having at least 90%, at least 95%, at least 98% or at least 99% sequence identity;

the CDRH2 region comprises the amino acid sequence of SEQ ID NO: 5, or a substantially similar sequence thereof having at least 90%, at least 95%, at least 98% or at least 99% sequence identity;

the CDRH3 region comprises the amino acid sequence of SEQ ID NO: 6, or a substantially similar sequence thereof having at least 90%, at least 95%, at least 98% or at least 99% sequence identity;

the CDRL1 region comprises the amino acid sequence of SEQ ID NO: 7, or a substantially similar sequence thereof having at least 90%, at least 95%, at least 98% or at least 99% sequence identity;

the CDRL2 region comprises the amino acid sequence of SEQ ID NO: 8, or a substantially similar sequence thereof having at least 90%, at least 95%, at least 98% or at least 99% sequence identity; and the CDRL3 region comprises the amino acid sequence of SEQ ID NO: 9, or a substantially similar sequence thereof having at least 90%, at least 95%, at least 98% or at least 99% sequence identity.

In one another preferred embodiment of the invention, the antibody or antigen-binding fragment thereof comprises complementarity determining regions of a heavy chain variable region and complementarity determining regions of a light chain variable region, wherein the complementarity determining regions of the heavy chain variable region comprises CDRH1, CDRH2 and CDRH3 regions, and the complementarity determining regions of the light chain variable region comprises CDRL1, CDRL2 and CDRL3 regions, and the CDRH1 region comprises the amino acid sequence of SEQ ID NO: 10, or a substantially similar sequence thereof having at least 90%, at least 95%, at least 98% or at least 99% sequence identity;

the CDRH2 region comprises the amino acid sequence of SEQ ID NO: 11, or a substantially similar sequence thereof having at least 90%, at least 95%, at least 98% or at least 99% sequence identity;

the CDRH3 region comprises the amino acid sequence of SEQ ID NO: 12, or a substantially similar sequence thereof having at least 90%, at least 95%, at least 98% or at least 99% sequence identity;

the CDRL1 region comprises the amino acid sequence of SEQ ID NO: 13, or a substantially similar sequence thereof having at least 90%, at least 95%, at least 98% or at least 99% sequence identity;

the CDRL2 region comprises the amino acid sequence of SEQ ID NO: 14, or a substantially similar sequence thereof having at least 90%, at least 95%, at least 98% or at least 99% sequence identity; and the CDRL3 region comprises the amino acid sequence of SEQ ID NO: 15, or a substantially similar sequence thereof having at least 90%, at least 95%, at least 98% or at least 99% sequence identity.

In one preferred embodiment of the invention, an antibody 322A6 or antigen-binding fragment thereof comprises a heavy chain variable region comprising the amino acid sequences of SEQ ID NO: 17 or a substantially similar sequence thereof having at least 90%, at least 95%, at least 98% or at least 99% sequence identity. Preferably, the heavy chain variable region is encoded by a nucleic acid sequence of SEQ ID NO: 16. The 322A6 or antigen-binding fragment thereof comprises a light chain variable region comprising the amino acid sequence of SEQ ID NO: 19 or a substantially similar sequence thereof having at least 90%, at least 95%, at least 98% or at least 99% sequence identity or a substantially similar sequence thereof. Preferably, the light chain variable region is encoded by a nucleic acid sequence of SEQ ID NO: 18.

In one preferred embodiment of the invention, an antibody 12A6 or antigen-binding fragment thereof comprises a heavy chain variable region comprising the amino acid sequences of SEQ ID NO: 21 or a substantially similar sequence thereof having at least 90%, at least 95%, at least 98% or at least 99% sequence identity. Preferably, the heavy chain variable region is encoded by a nucleic acid sequence of SEQ ID NO: 20. The 12A6 or antigen-binding fragment thereof comprises a light chain variable region comprising the amino acid sequence of SEQ ID NO: 23 or a substantially similar sequence thereof having at least 90%, at least 95%, at least 98% or at least 99% sequence identity or a substantially similar sequence thereof. Preferably, the light chain variable region is encoded by a nucleic acid sequence of SEQ ID NO: 22.

In another aspect, the antibody according to the invention is preferably a humanized antibody. A "humanized antibody" is a recombinant protein in which the CDRs from an antibody from one species; e.g., a rodent antibody, are transferred from the heavy and light variable chains of the rodent antibody into human heavy and light variable domains, including human framework region (FR) sequences. The constant domains of the antibody molecule are derived from those of a human antibody.

In order to improve the binding affinity of the humanized antibody according to the invention, some amino acid residues in the human framework region are replaced by the corresponding amino acid residues in the species of CDRs; e.g. a rodent. Preferably, a humanized antibody Hu322B1HdH or antigen-binding fragment thereof comprises a heavy chain variable region comprising the amino acid sequences of SEQ ID NO: 25 or a substantially similar sequence thereof having at least 90%, at least 95%, at least 98% or at least 99% sequence identity. Preferably, the heavy chain variable region is encoded by a nucleic acid sequence of SEQ ID NO: 24. The Hu322B1HdH or antigen-binding fragment thereof comprises a light chain variable region comprising the amino acid sequence of SEQ ID NO: 27 or a substantially similar sequence thereof having at least 90%, at least 95%, at least 98% or at least 99% sequence identity or a substantially similar sequence thereof. Preferably, the light chain variable region is encoded by a nucleic acid sequence of SEQ ID NO: 26.

Preferably, the antibody according to the invention is a monoclonal antibody.

The antibodies of the present invention may be mono-specific, bi-specific, or multispecific. Multispecific antibodies may be specific for different epitopes of one target polypeptide or may contain antigen-binding domains specific for more than one target polypeptide. The anti-VEGFR-2 antibodies of the present invention can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multispecific antibody with a second binding specificity. For example, the present invention includes bi-specific antibodies wherein one arm of an immunoglobulin is specific for human VEGFR-2 or a fragment thereof, and the other arm of the immunoglobulin is specific for a second therapeutic target or is conjugated to a therapeutic moiety.

In one preferred embodiment of the invention, the antibody or antigen-binding fragment thereof is conjugated with a therapeutic agent.

As used herein, a "therapeutic agent" represents a cytostatic or cytotoxic agent or an isotope-chelating agent with corresponding radioisotopes. Examples of the cytostatic or cytotoxic agent include, without limitation, antimetabolites (e.g., fluorouracil (5-FU), floxuridine (5-FUdR), methotrexate, leucovorin, hydroxyurea, thioguanine (6-TG), mercaptopurine (6-MP), cytarabine, pentostatin, fludarabine phosphate, cladribine (2-CDA), asparaginase, gemcitabine, capecitibine, azathioprine, cytosine methotrexate, trimethoprim, pyrimethamine, or pemetrexed); alkylating agents (e.g., cmelphalan, chlorambucil, busulfan, thiotepa, ifosfamide, carmustine, lomustine, semustine, streptozocin, dacarbazine, mitomycin C, cyclophosphamide, mechlorethamine, uramustine, dibromomannitol, tetranitrate, procarbazine, altretamine, mitozolomide, or temozolomide); alkylating-like agents (e.g., cisplatin, carboplatin, nedaplatin, oxaliplatin, satraplatin, or triplatin); DNA minor groove alkylating agents (e.g., duocarmycins such as CC-1065, and any analogs or derivatives thereof; pyrrolobenzodiazapenes, or any analogs or derivatives thereof); anthracyclines (e.g., daunorubicin, doxorubicin, epirubicin, idarubicin, or valrubicin); antibiotics (e.g., dactinomycin, bleomycin, mithramycin, anthramycin, streptozotocin, gramicidin D, mitomycins (e.g., mitomycin C); calicheamicins; antimitotic agents (including, e.g., maytansinoids (such as DM1, DM3, and DM4), auristatins (including, e.g., monomethyl auristatin E (MMAE) and monomethyl auristatin F (MMAF)), dolastatins, cryptophycins, vinca alkaloids (e.g., vincristine, vinblastine, vindesine, vinorelbine), taxanes (e.g., paclitaxel, docetaxel, or a novel taxane), tubulysins, and colchicines); topoisomerase inhibitors (e.g., irinotecan, topotecan, camptothecin, etoposide, teniposide, amsacrine, or mitoxantrone); HDAC inhibitor (e.g., vorinostat, romidepsin, chidamide, panobinostat, or belinostat); proteasome inhibitors (e.g., peptidyl boronic acids); as well as radioisotopes such as $At^{211}$, $I^{131}$, $I^{125}$, $Y^{90}$, $Re^{186}$, $Re^{188}$, $Sm^{153}$, $Bi^{212}$ or $^{213}$, $P^{32}$ and radioactive isotopes of Lu including $Lu^{177}$. Examples of the isotope-chelating agents include, without limitation, ethylenediaminetetraacetic acid (EDTA), diethylenetriamine-N,N,N',N'',N''-pentaacetate (DTPA), 1,4,7,10-tetraazacyclododecane-N,N',N'',N'''-tetraacetate (DOTA), 1,4,7,10-tetrakis(2-hydroxypropyl)-1,4,7,10-tetraazacyclododecane (TH P), triethylenetetraamine-N,N,N', N'',N''',N'''-hexaacetate (TTHA), 1,4,7,10-tetraazacyclododecane-N,N',N'',N'''-tetrakis(methylenephosphonate) (DOTP), and mercaptoacetyltriglycine (MAG3).

In one preferred embodiment of the invention, the antibody or antigen-binding fragment thereof can be produced using any number of expression systems, including prokaryotic and eukaryotic expression systems. In some embodiments, the expression system is a mammalian cell expression, such as a hybridoma, or a CHO cell expression system. Many such systems are widely available from commercial suppliers. In embodiments in which an antibody comprises both a $V_H$ and $V_L$ region, the $V_H$, and $V_L$ regions may be expressed using a single vector, e.g., in a di-cistronic expression unit, or under the control of different promoters. In other embodiments, the $V_H$ and $V_L$ region may be expressed using separate vectors. A $V_H$ or $V_L$ region as described herein may optionally comprise a methionine at the N-terminus.

The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, Immunology (3.sup.rd ed. 1997)).

Techniques for the production of single chain antibodies or recombinant antibodies (U.S. Pat. No. 4,946,778, U.S. Pat. No. 4,816,567) can be adapted to produce antibodies to polypeptides of this invention. Also, transgenic mice, or other organisms such as other mammals, can be used to express humanized or human antibodies (see, e.g., U.S. Pat. Nos. 5,545,807; 5,545,806; 5,569,825; 5,625,126; 5,633,425; 5,661,016, Marks et al., Bio/Technology 10:779-783 (1992); Lonberg et al., Nature 368:856-859 (1994); Morrison, Nature 368:812-13 (1994); Fishwild et al., Nature Biotechnology 14:845-51 (1996); Neuberger, Nature Biotechnology 14:826 (1996); and Lonberg & Huszar, Intern. Rev. Immunol. 13:65-93 (1995)).

In one preferred embodiment of the invention, the antibody or antigen-binding fragment thereof is expressed on a surface of a cell. More preferably, the cell is a T-cell.

The invention provides pharmaceutical compositions comprising the anti-VEGFR-2 antibody or antigen-binding fragment thereof of the present invention. The pharmaceutical compositions of the invention are formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™, Life Technologies, Carlsbad, Calif.). DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody administered to a patient may vary depending upon the age and the size of the patient, target disease, conditions, route of administration, and the like. The preferred dose is typically calculated according to body weight or body surface area. When an antibody of the present invention is used for treating a condition or disease associated with VEGFR-2 activity in an adult patient, it may be advantageous to intravenously administer the antibody of the present invention normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted. Effective dosages and schedules for administering anti-VEGFR-2 antibody may be determined empirically; for example, patient progress can be monitored by periodic assessment, and the dose adjusted accordingly. Moreover, interspecies scaling of dosages can be performed using well-known methods in the art (e.g., Mordenti et al., 1991, Pharmaceut. Res. 8:1351).

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see. Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

The antibody according to the invention is useful for inhibiting VEGFR-mediated signaling and for treating diseases and disorders caused by or related to VEGFR-2 activity and/or signaling. The antibody of the invention is also useful for inhibiting cell proliferation of endothelial cells.

The present invention provides a method for inhibiting VEGFR-2-mediated signaling in a subject in need, comprising administering to the subject a pharmaceutical composition comprising the antibody or antigen-binding fragment thereof as mentioned above.

The present invention provides a method for treating diseases and/or disorders caused by or related to VEGFR-2 activity and/or signaling in a subject afflicted with the diseases and/or disorders, comprising administering to the subject a pharmaceutical composition comprising the antibody or antigen-binding fragment thereof as mentioned above.

The present invention provides a method for treating tumor in a subject afflicted with the tumor, comprising administering to the subject a pharmaceutical composition comprising the antibody or antigen-binding fragment thereof as mentioned above.

The present invention provides a method for inhibiting cell proliferation of endothelial cells in a subject in need, comprising administering to the subject a pharmaceutical composition comprising the antibody or antigen-binding fragment thereof as mentioned above.

The terms "treating" and "treatment" as used herein refer to the administration of an agent or formulation to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage. The terms "preventing" and "prevention" refer to the administration of an agent or composition to a clinically asymptomatic individual who is susceptible to a particular adverse condition, disorder, or disease, and thus relates to the prevention of the occurrence of symptoms and/or their underlying cause. As is understood by one skilled in the art, prevention or preventing need not achieve absolute (complete) block or avoidance of the conditions. Rather, prevention may achieve substantial (e.g., over about 50%) reduction or avoidance of the diseases or conditions to be prevented. Unless otherwise indicated herein, either explicitly or by implication, if the term "treatment" (or "treating") is used without reference to possible prevention, it is intended that prevention be encompassed as well.

"Cancer," "tumor," "transformed" and like terms include precancerous, neoplastic, transformed, and cancerous cells, and can refer to a solid tumor, or a non-solid cancer (see, e.g., Edge et al. AJCC Cancer Staging Manual (7th ed. 2009); Cibas and Ducatman Cytology: Diagnostic principles and clinical correlates (3rd ed. 2009)). Cancer includes both benign and malignant neoplasms (abnormal growth). "Transformation" refers to spontaneous or induced phenotypic changes, e.g., immortalization of cells, morphological changes, aberrant cell growth, reduced contact inhibition and anchorage, and/or malignancy (see, Freshney, Culture of Animal Cells a Manual of Basic Technique (3rd ed. 1994)). Although transformation can arise from infection with a transforming virus and incorporation of new genomic DNA, or uptake of exogenous DNA, it can also arise spontaneously or following exposure to a carcinogen.

The antibody of the invention is useful, inter alia, for the treatment, prevention and/or amelioration of any disease or disorder associated with or mediated by VEGFR-2 expression or activity, or treatable by blocking the interaction between VEGFR-2 and a VEGFR-2 ligand or otherwise inhibiting VEGFR-2 activity and/or signaling, and/or promoting receptor internalization and/or decreasing cell surface receptor number. For example, the antibody and antigen-binding fragment of the present invention are useful for the treatment of tumors that express high levels of VEGFR-2. The antibody and antigen-binding fragment of the present invention may be used to treat, e.g., primary and/or metastatic tumors arising in the brain and meninges, oropharynx, lung and bronchial tree, gastrointestinal tract, male and female reproductive tract, muscle, bone, skin and appendages, connective tissue, spleen, immune system, blood forming cells and bone marrow, liver and urinary tract, and special sensory organs such as the eye. In certain embodiments, the antibody and antigen-binding fragment of the invention are used to treat one or more of the following cancers: renal cell carcinoma, pancreatic carcinoma, breast cancer, head and neck cancer, prostate cancer, malignant gliomas, osteosarcoma, colorectal cancer, gastric cancer (e.g., gastric cancer with MET amplification), malignant mesothelioma, multiple myeloma, ovarian cancer, small cell lung cancer, non-small cell lung cancer (e.g., VEGFR-2-dependent non-small cell lung cancer), synovial sarcoma, thyroid cancer, or melanoma.

The present invention provides a method for detecting human vascular endothelial growth factor receptor in a sample comprising contacting the sample with the antibody or antigen-binding fragment thereof as mentioned above.

The anti-VEGFR-2 antibody of the present invention may also be used to detect and/or measure VEGFR-2, or VEGFR-2-expressing cells in a sample, e.g., for diagnostic purposes. For example, an anti-VEGFR-2 antibody, or fragment thereof, may be used to diagnose a condition or disease characterized by aberrant expression (e.g., over-expression, under-expression, lack of expression, etc.) of VEGFR-2. Exemplary diagnostic assays for VEGFR-2 may comprise, e.g., contacting a sample, obtained from a patient, with an anti-VEGFR-2 antibody of the invention, wherein the anti-VEGFR-2 antibody is labeled with a detectable label or reporter molecule. Alternatively, an unlabeled anti-VEGFR-2 antibody can be used in diagnostic applications in combination with a secondary antibody which is itself detectably labeled. The detectable label or reporter molecule can be a radioisotope, such as $^{3}H$, $^{14}C$, $^{32}P$, $^{35}S$, or $^{125}I$; a fluorescent or chemiluminescent moiety such as fluorescein isothiocyanate, or rhodamine; or an enzyme such as alkaline phosphatase, beta-galactosidase, horseradish peroxidase, or luciferase. Specific exemplary assays that can be used to detect or measure VEGFR-2 in a sample include enzyme-linked immunosorbent assay (ELISA), radioimmunoassay (RIA), and fluorescence-activated cell sorting (FACS).

Samples that can be used in VEGFR-2 diagnostic assays according to the present invention include any tissue or fluid sample obtainable from a patient which contains detectable quantities of VEGFR-2 protein, or fragments thereof, under normal or pathological conditions. Generally, levels of VEGFR-2 in a particular sample obtained from a healthy patient (e.g., a patient not afflicted with a disease or condition associated with abnormal VEGFR-2 levels or activity) will be measured to initially establish a baseline, or standard, level of VEGFR-2. This baseline level of VEGFR-2 can then be compared against the levels of VEGFR-2 measured in samples obtained from individuals suspected of having a VEGFR-2 related disease or condition.

The following examples are provided to aid those skilled in the art in practicing the present invention.

EXAMPLES

Construction of scFv/Fab Antibody Library

VEGFR2-Fc-His, a fusion protein containing the sequence of SEQ ID NO: 1 was used as an antigen to immune a mouse 6 times every two weeks. After immunization, the mouse was sacrificed and the spleen was obtained. Total RNAs of the spleen were extracted and reverse transcribed in an RT-PCR procedure with the primers to construct antibody fragments containing $V_H$, $V_L$, $V_H$-CH1, $V_L$-CL. The antibody fragments were assembled into scFv fragments in polymerase chain reactions and a scFv library was constructed. To begin with, the Fab library was constructed with a $V_L$-CL library from $V_L$-CL fragments into a plasmid. Next, $V_H$-CH1 fragments were constructed into the plasmid containing the $V_L$-CL fragments to general the final Fab library.

Preparation of scFv/Fab Phage for Bio-Panning

The obtained library was inoculated into a 2×YT medium containing 100 µg/ml ampicillin and 2% glucose (2YTAG) and incubated with shaking at 37° C. until the OD at 600 nm reaching 0.5. The culture was infected with a helper phage and then cultured without shaking in a 37° C. water bath for 30 min. The cells were collected and suspended in a 2×YT medium containing 100 µg/ml ampicillin and 25 µg/ml kanamycin (2YTAK) and further incubated with shaking at 30° C. overnight. The supernatant of the culture was collected and mixed with 1/5 volume of PEG/NaCl (20% Polyethylene glycol 8000, 2.5 M NaCl) and stayed for 1 hr or more at 4° C. After centrifuging, the pellet was collected and suspended in 40 mL of PBS and spun again to collect the supernatant.

Selection Using ELISA Method

An ELISA plate (Nunc) was coated with 1 µg/100 µL of antigen per well and stayed in sodium bicarbonate buffer, pH 9.6 at 4° C. overnight. The wells were washed 3 times with PBS and blocked with 300 µL of PBS-5% skim milk (MPBS) per well at 37° C. for 1.5 hr. After washed 3 times with PBS, 100 µL of phages in 5% MPBS with fusion protein contains his-tag were added and incubated at 37° C. for 90 min. After washed 10 times with PBS-0.05% Tween 20 (PBST) and 10 times PBS, the phages were eluted by adding 100 µL of 100 mM triethylamine (TEA) and reacted at 37° C. for 30 min. One-hundred µL of eluted phages were neutralized with 50 µL of 1 M Tris, pH 7.4. Ten ml of TG1 at an exponentially growing stage were added to 150 µL of the eluted phages. The cultures were incubated at 37° C. for 30 min without shaking for infection. The infected TG1 bacteria were spun and collected and then suspended in 2×YT and plated on a 2×YT-AG plate. The bacteria were incubated at 30° C. overnight.

Selection Using Dynabeads Method

In a pre-clean phage step, Dynabeads were pre-washed with 1 ml of PBS three times, and suspended in PBS. Then, 0.3 mL of the phages were mixed with 0.5 ml of 5% MPBS, fusion protein contains his-tag and incubated on a rotator for 30 min, and then Dynabeads were removed.

The Dynabeads were reacted with biotin-labeled VEGFR2-His for 90 min. The Dynabeads were washed with 1 ml of PBS three times and suspended in 5% MPBS and incubated for 90 min and then washed with 1 ml of PBS three times. The pre-clean phage was added to the VEGFR2-His with Dynabeads and incubated on a rotator for another 30 min. The Dynabeads were then washed with 1 ml of 0.05% PBST, 0.2% MPBS, and PBS. The bound phages were eluted with 1 ml of 100 mM TEA. For quick neutralization, 0.5 ml of IM Tris, pH 7.4 was added to the eluted phages. Then, 6 ml of an exponentially growing culture of TG1 was taken and the TEA eluted phages were added. The cultures were incubated for 30 min at 37° C. (water bath) without shaking. The infected TG1 bacterial were pooled and spun for collecting the pellet. The pelleted bacteria were suspended in 1 ml of 2×YT and plated on a large 2×YT-AG plate. The bacteria were incubated at 30° C. overnight.

Preparation of Next Round Phage

Five to six ml of 2×YT, 15% glycerol was added to the bacterial plate and the colonies were loosed with a glass spreader. Then, 10 µl of the scraped bacteria were added to 10 ml of 2×YT-AG and the bacteria grew with shaking at 37° C. until the OD at 600 nm reaching 0.5. Ten ml of the culture was infected with M13KO7 helper phage by adding the helper phage in the ratio of 1:20 and the infected culture was incubated without shaking in a 37° C. water bath for 30 min. The cultures were spun to collect the pellet, and the pellet was suspension with 50 mL of 2×YT-AK and then cultured at 30° C. overnight. Further, 40 ml of the overnight culture was spun at 10,000 rpm for 20 min to collect the supernatant, and 1/5 volume (8 ml) PEG/NaCl was added to the supernatant. The well was mixed and left for 1 hr or more at 4° C. The mixture was spun at 10,000 rpm for 20 min and the pellet was collected and suspended in 2 ml PBS. The suspension was spun at 12000 rpm for 10 min to remove most of the remaining bacterial debris.

Screening of VEGFR2-Positive Phage by ELISA

The individual colonies from the plate were inoculated into 200 μl of 2×YT-AG 96-well plates and grew with shaking overnight at 37° C. and then 50 ul transferred to a second 96-well plate containing 200 μl of 2×YT-AG per well for shaking at 37° C. for 2 hr. Then, 50 μl of 2×YT-AG with $10^9$ pfu M13KO7 helper phage was added to each well of the second plate. The mixture was stood for 30 min at 37° C. and then shaken for 1 hr at 37° C. After spun at 4000 rpm for 30 min, and the supernatant was aspirated off, and the pellet was suspended in 300 μl of 2×YT-AK for growing with shaking overnight at 30° C. The culture was spun at 4000 rpm for 30 min and 100 μl of the culture supernatant was taken for phage ELISA.

The ELISA plates were coated with 1 μg/mL per well of protein antigen, and then rinsed 3 times with PBS, and blocked with 300 μl of 2% MPBS per well for 2 hr at 37° C. After further rinsed 3 times with PBS, 100 μl phage culture supernatant as detailed above was added and incubated for 90 min at 37° C. The phage solution was discarded and the wells were washed 6 times with PBST and 6 times with PBS then an appropriate dilution of HRP-anti-M13 antibody in 5% MPBS was added. The mixture was incubated for 60 min at 37° C., and washed 6 times with PBST and 6 times with PBS. The wells were developed with substrate solution (TMB) and the reactions were stopped by adding 50 μp of 1 M sulfuric acid. The color turned yellow, and the OD at 650 nm and at 450 nm was assayed.

After screening, total 379 clones and 66 kinds of CDRH3 are identified.

Expression of Full-Length Antibodies

The genes encoding the $V_H$ and $V_L$ chains of anti-VEGFR2 antibodies were inserted into an expression vector. Free-style 293 cells were transfected with the vector constructed. Follow the procedure below to transfect suspension FreeStyle™ 293 cells in a 30 ml volume. Approximately 24 hrs before transfection, pass FreeStyle™ 293 cells at $2 \times 10^6$ cells/ml for 15 ml. Place the flask(s) at 37° C., 8% $CO_2$ incubator. Then dilute 37.5 μg of plasmid DNA into 1.5 ml of sterile 150 mM NaCl to a total volume of 1.5 ml. In a separate tube, dilute 37.5 μL of PEI (2.0 mg/ml) in 1.5 ml of sterile 150 mM NaCl. Stand DNA and PEI solution at room temp for 5 minutes, mix gently by inverting the tube and stand at room temp around 10-20 minutes. Immediately add DNA-PEI mixture into F293 cells and incubate transfected cells on an orbital shaker platform rotating at 135-150 rpm at 37° C., 8% CO2 incubator for 4 hours. Then add equal volume fresh culture medium to a total volume of 30 ml and culture during 5-7 days. Cells were harvested for protein purification and quantification.

Total 78 colonies are identified, including 322A6 and 12A6.

Binding Affinity Assay

An ELSA plate was coated with 100 μL per well of human VEGFR-2, mouse VEGFR2, human VEGFR1 or human VEGFR3 overnight at 4° C., and then rinsed 3 times with PBS and blocked with 300 μL per well of 5% MPBS for 2 hr at 37° C. The wells were rinsed 3 times with PBS, and 100 μL of anti-VEGFR2 antibody, 2 fold serial dilutions, was added and incubated for 90 min at 37° C. The test solution was discarded and washed 3 times with PBS. Appropriate dilution of HRP-anti-Human IgG antibody in 5% MPBS (1:10000) was added and incubated for 60 min at 37° C., and the wells were washed 3 times with PBS. The wells were developed with 100 μL of substrate solution TMB and the reactions were terminated by adding 50 μL of 1 M sulfuric acid. The color turned yellow and the OD at 650 nm and at 450 nm was assayed.

The results of binding affinity of several antibodies are shown in FIG. 1 and Table 1. It shows that 12A6 and 322A6 antibodies have binding affinity to human VEGFR-2. 322A6 antibody has binding affinity to mouse VEGFR-2, but has no affinity to human VEGFR-1 and VEGFR-3. Thus, 322A6 is specific to VEGFR-2.

TABLE 1

| | VEGFR-2 (domains 1 to 7) | | | | |
|---|---|---|---|---|---|
| Analyte Antibodies | $K_a$ | $K_d$ | $K_D$ | Rmax (RU) | Chi$^2$ (RU$^2$) |
| 12A6 | 4.488E+4 | 2.066E−4 | 4.604E−9 | 276.9 | 0.457 |
| 322A6 | 8.247E+5 | 5.547E−4 | 6.726E−10 | 102.2 | 4.29 |

The sequences of CDRs of 322A6 and 12A6 are shown in Table 2. 322A6 comprises a heavy chain variable region comprising the amino acid sequences of SEQ ID NO: 17, and the heavy chain variable region is encoded by a nucleic acid sequence of SEQ ID NO: 16. 322A6 comprises a light chain variable region comprises the amino acid sequence of SEQ ID NO: 19, and the light chain variable region is encoded by a nucleic acid sequence of SEQ ID NO: 18. 12A6 comprises a heavy chain variable region comprising the amino acid sequences of SEQ ID NO: 21, and the heavy chain variable region is encoded by a nucleic acid sequence of SEQ ID NO: 20. 12A6 comprises a light chain variable region comprises the amino acid sequence of SEQ ID NO: 23, and the light chain variable region is encoded by a nucleic acid sequence of SEQ ID NO: 22.

TABLE 2

| Sample | CDRH1 | CDRH2 | CDRH3 | CDRL1 | CDRL2 | CDRL3 |
|---|---|---|---|---|---|---|
| 322A6 | GYAFTMIDFSDS TYWMHETKLNQR FKG (SEQ ID NO: 4) | (SEQ ID NO: 5) | DVRGNF DV (SEQ ID NO: 6) | RASKSVS TSGYSYM H (SEQ ID NO: 7) | LASNLES (SEQ ID NO: 8) | QHSRELP WT (SEQ ID NO: 9) |
| 12A6 | GYSFTYIDPYND DYSMYDTSYKQK FKG (SEQ ID NO: 10) | (SEQ ID NO: 11) | GYADAM DY (SEQ ID NO: 12) | HASQNIN VWLS (SEQ ID NO: 13) | KASNLHT (SEQ ID NO: 14) | QQGQSYP LT (SEQ ID NO: 15) |

Domain Mapping Assay

Figure 3B:
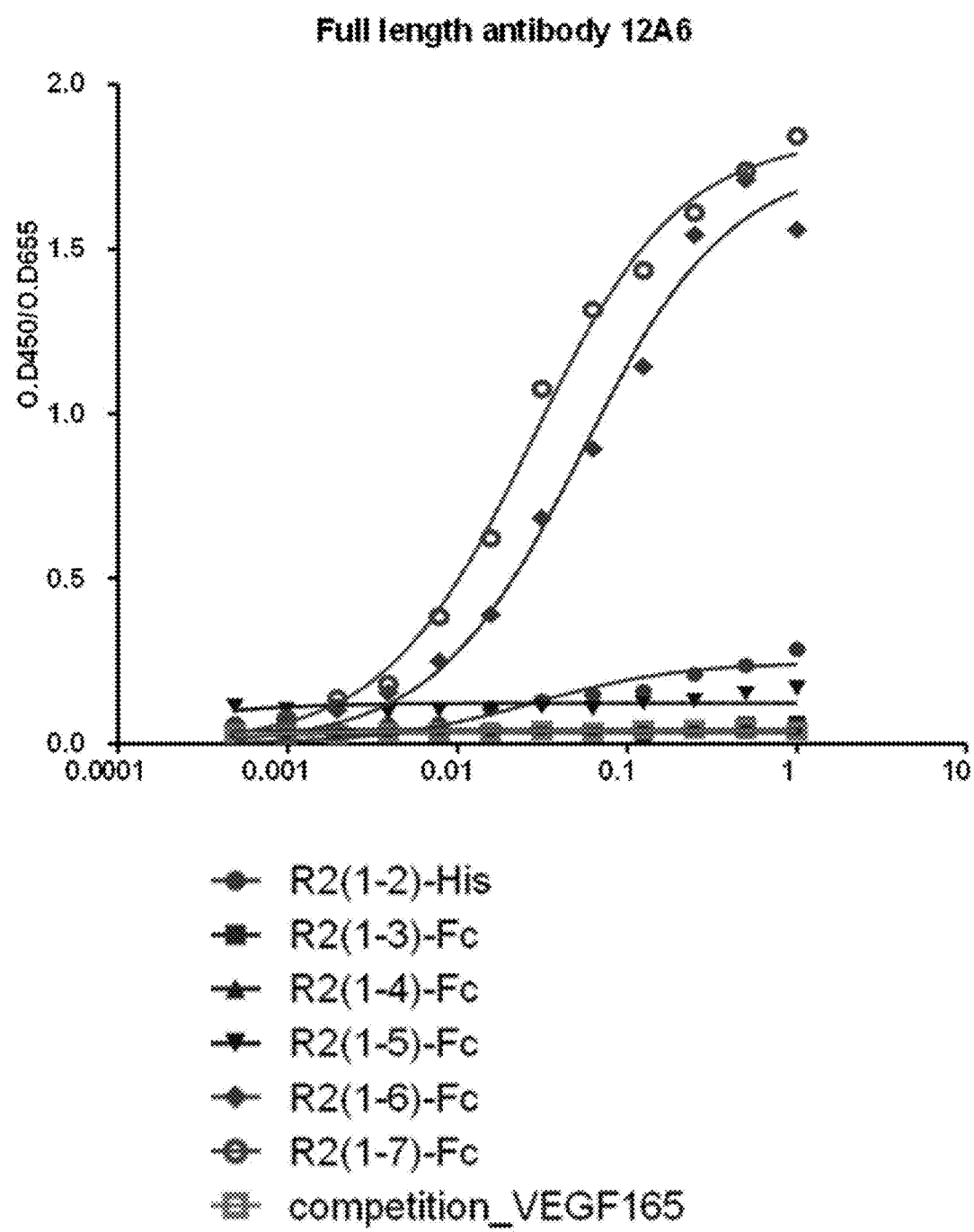
Figure 3C:
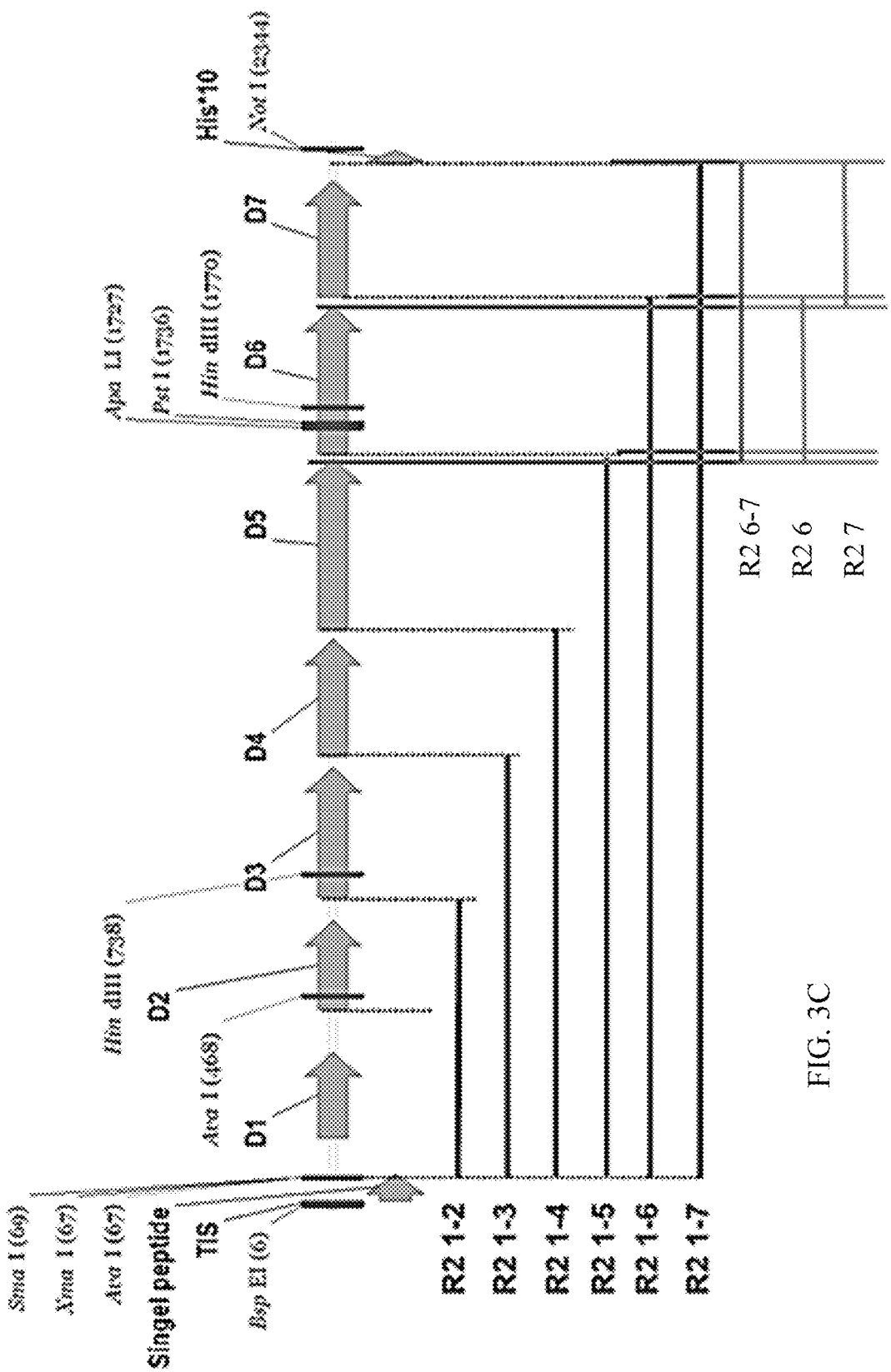

Fragments of human VEGFR-2 were constructed. The fragments were utilized to binding affinity assay as mentioned above. The result of domain mapping is shown in FIGS. 2 and 3 and Tables 3 and 4.

TABLE 3

| Binding domain | 322A6 (45) | 12A6 |
|---|---|---|
| R2 D1-2 | − | − |
| R2 D1-3 | − | − |
| R2 D1-4 | − | − |
| R2 D1-5 | − | − |
| R2 D1-6 | − | +++++ |
| R2 D1-7 | +++++ | +++++ |
| R2 D6-7 | +++++ | +++++ |
| R2 D6 | − | +++ |
| R2 D7 | ++++ | ++++ |

TABLE 4

| Sample | Binding Domain |
|---|---|
| 322A6 | 7 |
| 12A6 | 6-7 |

Epilope Mapping

Figure 4:
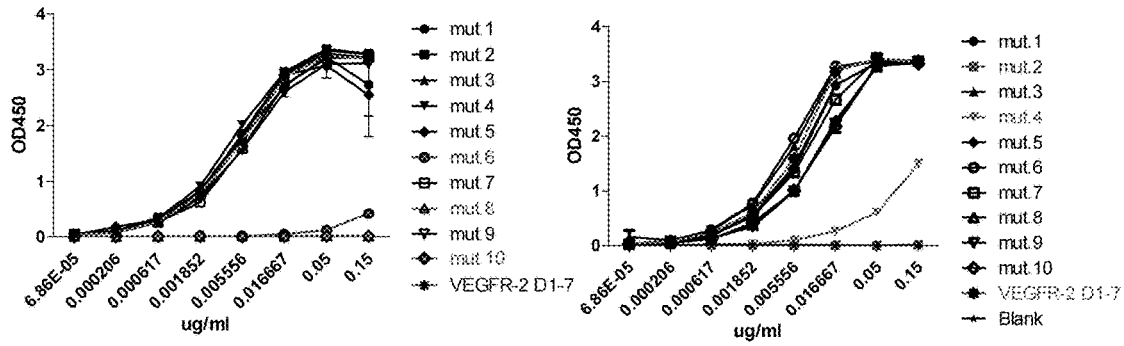
FIG. 4 shows the ELISA result of epitope mapping of the antibodies of the invention.

In domains 6 (SEQ ID NO: 2) and 7 (SEQ ID NO: 3) of human VEGFR-2, several point mutants were constructed. The mutants were utilized to binding affinity assay as mentioned above. The positions of the mutation sites are shown in FIG. 4. The epitope of 12A6 comprises the leucine residue at position 606, the aspartic acid residue at position 607, the arginine residue at position 647, the lysine residue at position 648, and the threonine residue at position 649. The epitope of 322A6 comprises the serine residue at position 711, the lysine residue at position 716, the aspartic acid residue at position 717, and the arginine residues at positions 725 and 726.

Anti-VEGF R2 Ab-HUVEC Proliferation Inhibition Assay

Materials: HUVEC (Cascade Biologics, Cat No. C-003-5C). Medium 200 (Cascade Biologics, Cat No. M-200-500), Hybridoma medium (10% FBS-DMEM), FBS (Hyclone, #SH30071.03), DMEM (GIBCO, #11995), Human CHO VEGF, hVEGF (PROSPEC, Cat No. CYT-260), anti-VEGFR2, WST-1 (Roche, Cat No. 11644807001).

One-hundred μL of antibody sample in 10% FBS-DMEM was inoculated to each well of a 96 well plate, and every sample was duplicated. The cells were harvested and suspended in Medium 200 at $8\times10^4$ cells/ml, and incubated for 30 mins at 37° C., 5% $CO_2$. The hVEGF was diluted in Medium 200 at 50 ng/ml, and 50 μL of standard hVEGF was added to the plate for incubating for 96 hours at 37° C., 5% $CO_2$. Then, 20 μL of WST-1 was added to each well and incubated for 4 hours at 37° C., 5% $CO_2$. The absorbance (OD450-655 nm) was measured using the ELISA reader.

Figure 5:
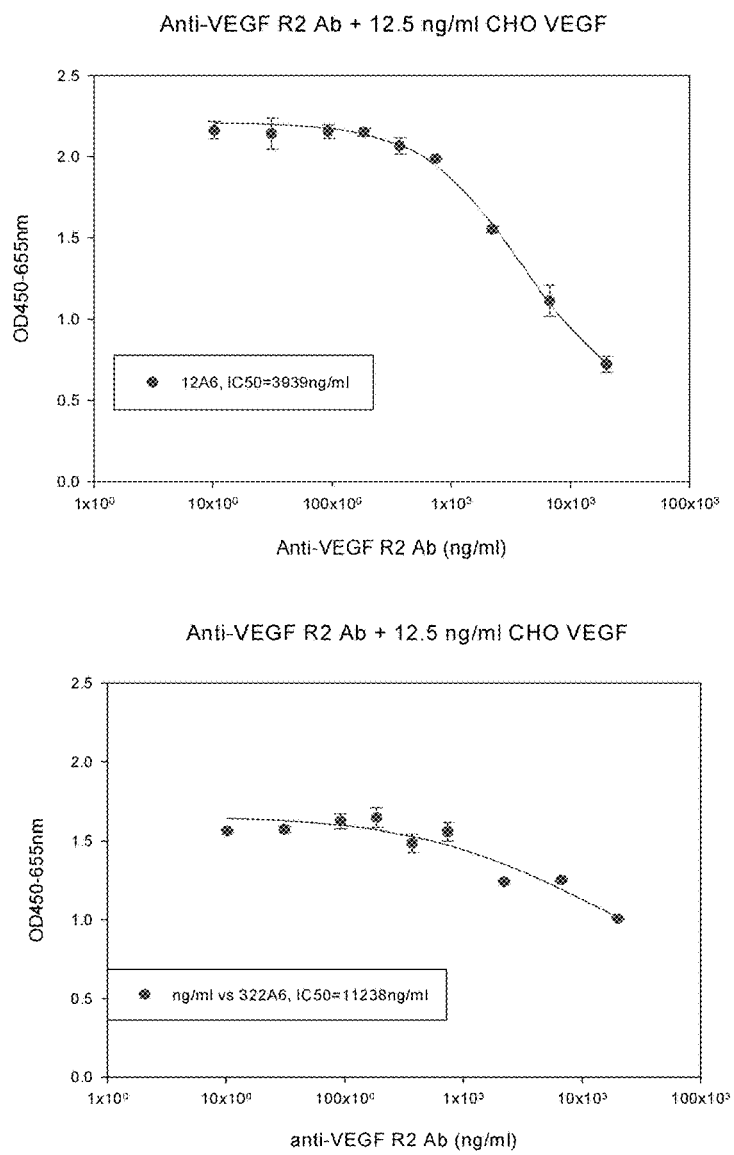
FIG. 5 shows the HUVEC proliferation inhibition assay of the antibodies of the invention.

The result of proliferation assay is shown in FIG. 5. As shown in FIG. 5, when the concentrations of the antibody are higher, the effect of VEGFR-2 signal inhibition is stronger, and the number of HUVEC (OD450-655 nm) is less. Among the antibodies, 12A6 has the strongest effect with IC50=3.9 μg/ml.

Internalization of Anti-VEGFR-2 Antibodies into HUVEC

The internalization of antibody into HUVECs was analyzed with the flow cytometry.
Flow cytometry (CytoFLEX)
Cell line: HUVEC
1 st Antibodies: 322A6
2nd Antibody: Goat anti-Human Kappa Light Chain, Bethyl, Cat.A80-115F
Medium 200 (M200), Thermo, Cat. C-003-25P-A, Low Serum Growth Supplement (LSGS). Cat.S00310
FBS (Gibco, Cat. 10082-147), FACS buffer (1×PBS, 1% FBS, 0.02% NaN3)
15-mL Falcon tube (Corning, Cat. CS352096)
T150: Tissue Culture Flasks (TPP, 90150)

The cell number of HUVEC was counted, and mixed with 322A6 and incubated on ice for 1 hr. The cells were collected by spinning and washed by 10 mL of ice-cold FACS buffer three times. $2\times10^5$ cells/rxn/well (24-well plate) were seeded in RPMI medium w/2% FBS, and then incubated at 37 C or 4° C. for indicated period. At each time point, the cells were washed by 10 mL of ice-cold FACS buffer, and 2nd antibody (α-hIgG-FITC, 1:200 diluted by ice-cold FACS buffer) was added on ice for 1 hr. After washed by 10 mL of ice-cold FACS buffer three times, the cells were seeded ($2*10^5$ cells/rxn/tube by FACS buffer) and incubated at 37 C or 4° C. for indicated period. At each time point, the cells were suspended and analyzed by Flow cytometry & CytExpert software.

Figure 6:
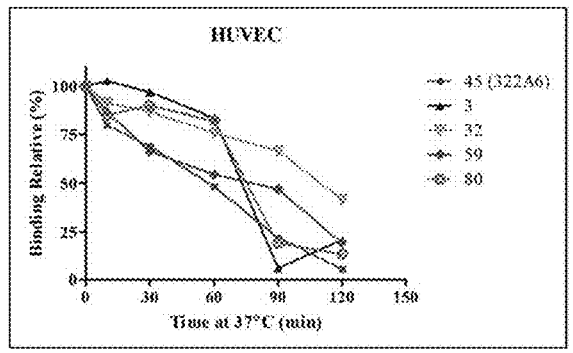
FIG. 6 shows the result of antibody internalization of the antibodies of the invention into HUVEC by flow cytometry.

The result is shown in Table 5 and FIG. 6. Before antibody internalization happening (0 min), the HUVEC cell bound with the antibody is detected with flow cytometry. After antibody internalization happening, the antibody is translocated from the surface of the cell to the endosome inside the cell, and the signal of flow cytometry disappears. Thus, if an antibody has strong tendency of antibody internalization, the relative binding with the target cell is lower. As can be seen in Table 5 and FIG. 6, 322A6 has the stronger tendency of antibody internalization.

TABLE 5

| | Cell population (%) | | | | |
|---|---|---|---|---|---|
| Time (min) | 322A6 | 3 | 32 | 59 | 80 |
| 0 | 31.4 | 18.1 | 38.7 | 31.1 | 39.9 |
| 10 | 25.1 | 18.6 | 35.3 | 27.0 | 34.0 |
| 30 | 21.6 | 17.5 | 33.7 | 20.6 | 35.9 |
| 60 | 15.1 | 15.1 | 29.3 | 17.0 | 32.9 |
| 90 | 6.8 | 1.1 | 25.7 | 14.6 | 7.5 |
| 120 | 1.7 | 3.7 | 16.1 | 5.9 | 5.2 |

Figure 7:
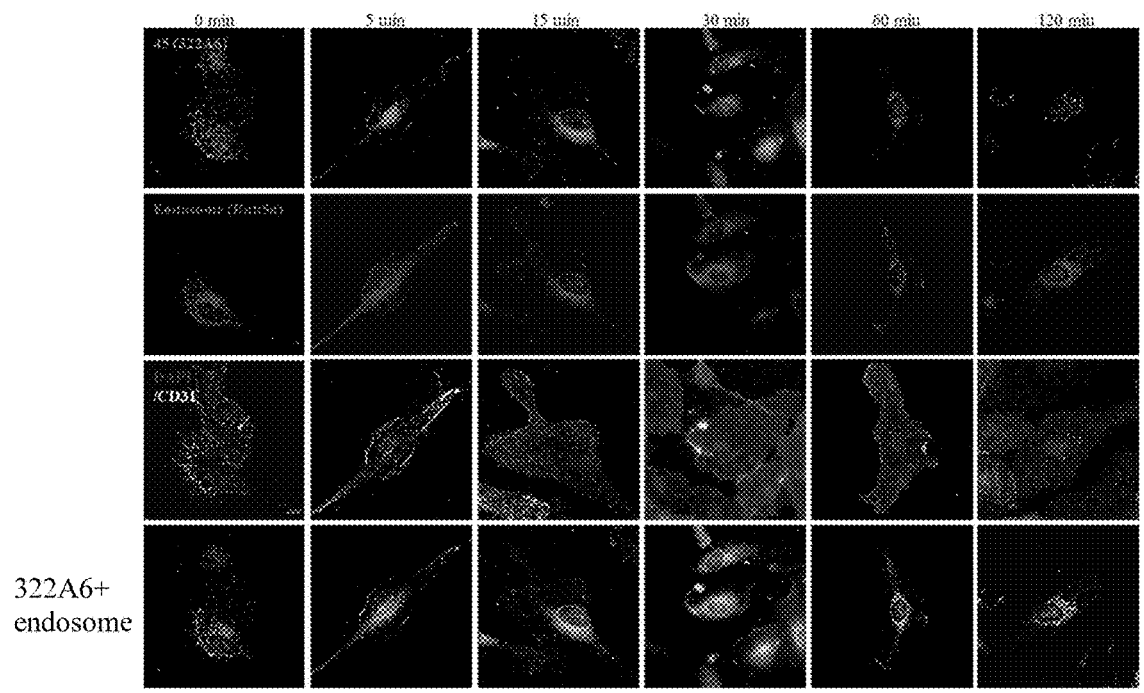
FIG. 7 shows the result of antibody internalization observed with the DeltaVision Microscopy Imaging System.

The antibody internalization was also observed under the microscope with the DeltaVision Microscopy Imaging System, and shown in FIG. 7. Rab5a was taken as a positive control, and DAPI was used for labeling nuclei. By labeling 322A6 and endosome simultaneously, it shows that 322A6 is successfully internalized into the cell.

Conjugation of Anti-VEGFR2 Antibody with Romidepsin

Figure 18:
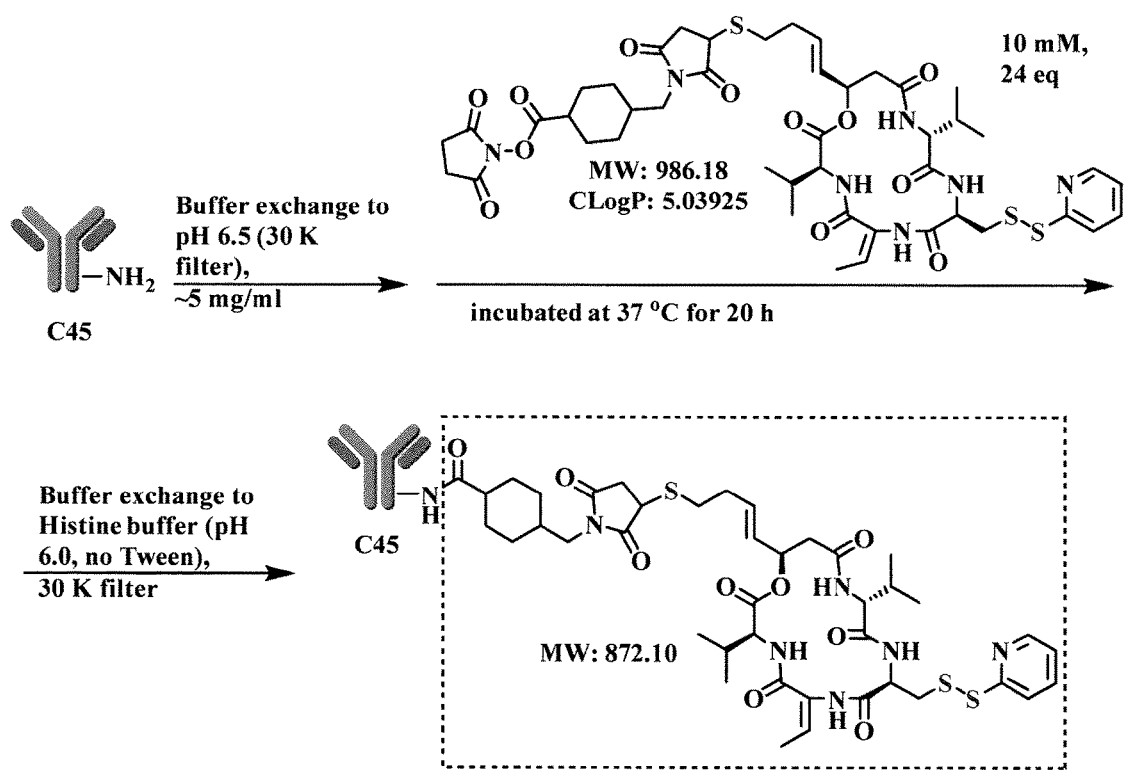
FIG. 18 shows a scheme for the conjugation of 322A6 (c45) antibody with Romidepsin.

322A6 (C45) antibody was conjugated with Romidepsin, also known as Istodax, an anticancer agent, according to the scheme shown in FIG. 18.

The condition of conjugation is listed in Table 6.

TABLE 6

| Lot No. | 322A6 | TMB355-SMCC-Romid-Spy | ADC (antibody-drug conjugate) |
|---|---|---|---|
| 14-0151-00-01 | 1 mg | SMCC-Romid-SPy(160413-1) in DMA: 10 mM, 24 eq Conc.: 5 mg/ml 37° C., 17 h | Conc: 4.06 □g/□l (Recovery rate: 73%) Aggregate: 2.1% DAR: 1.93 |

Figure 9:
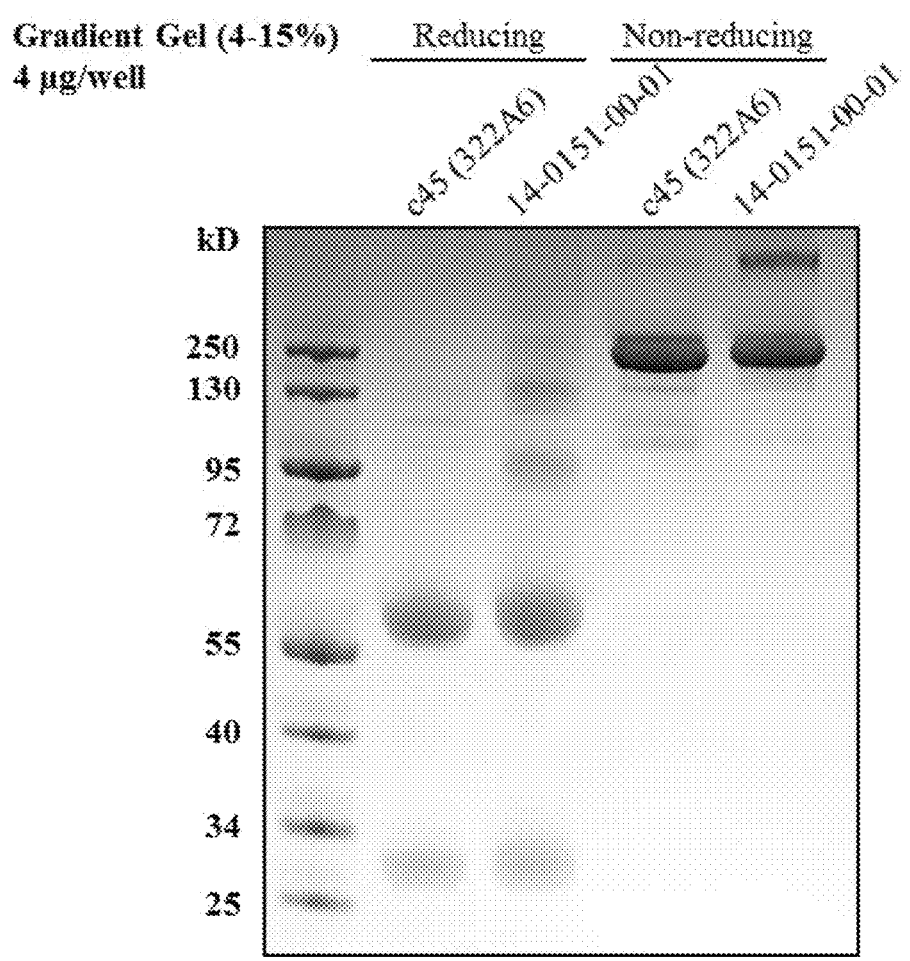
FIG. 9 shows the result of electrophoresis analysis of the antibody-drug conjugate according to the invention.

The obtained antibody-drug conjugate (ADC) (11-0151-00-01) was analyzed with size-exclusion chromatography (SEC):

Column: Superdex 200 Increase 10/300 GL (GE)
Sample: IgG & IgG-ADC, 0.3 mg/mL
Sample volume: 100 μL
Flow rate: 0.5 mL/min
Buffer: 1×PBS
System: ÄKTA The result of chromatography is shown in FIG. 8 and Table 7. The ADC was also subjected to electrophoresis and shown in FIG. 9.

TABLE 7

|  | c45 (322A6) | | 14-0151-00-01 (ADC of 322A6) | |
|---|---|---|---|---|
|  | Retention (mL) | Peak Area (%) | Retention (mL) | Peak Area (%) |
| Aggregates | — | 0.0 | 7.74 | 2.1 |
| IgG dimer | 10.61 | 3.3 | 10.42 | 6.0 |
| IgG Monomer | 12.46 | 95.4 | 12.34 | 91.3 |
| Fragments | 19.22 + 20.30 | 1.3 | 19.15 | 0.6 |

As shown in FIG. 8, the obtained antibody-drug conjugate has 95.4% of monomer and 95% of purity.

Figure 10:
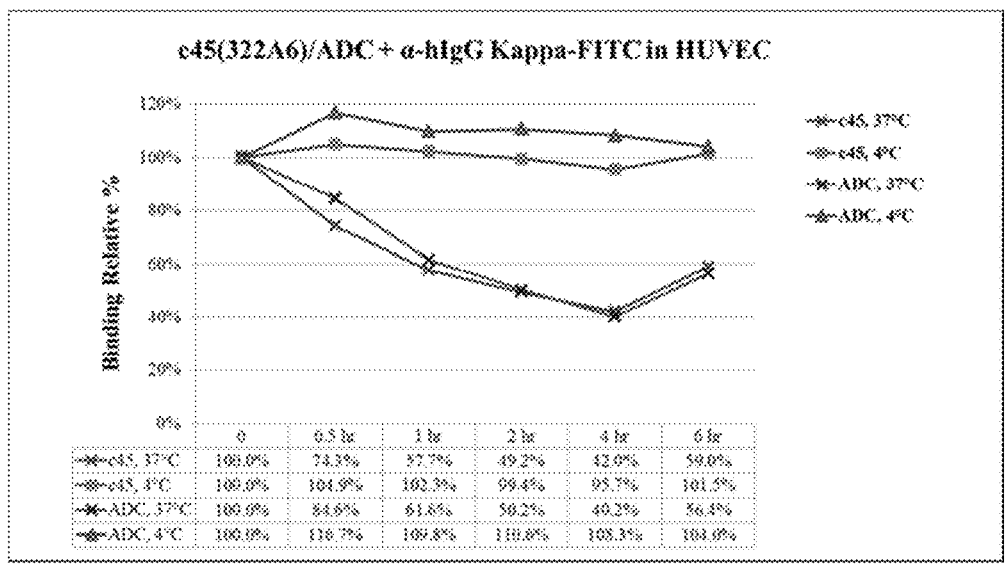
FIG. 10 shows the result of antibody internalization of the ADC according to the invention into HUVEC by flow cytometry.

The internalization of the ADC was also assayed as mentioned above. The result is shown in FIG. 10, and the tendency of internalization in the ADC of 322A6 is similar to that in 322 A6 antibody only (c45).

Figure 11:
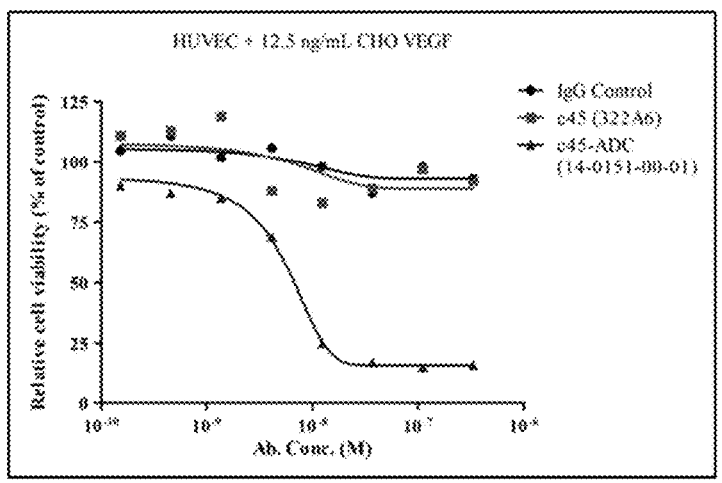
FIG. 11 shows the HUVEC proliferation inhibition assay of the ADC of the invention.

The inhibition of HUVEC proliferation of the ADC was also assayed as mentioned above. The result is shown in FIG. 11. The effect of 322A6 antibody only (c45) in inhibiting HUVEC proliferation was mild. It means that the blocking effect of 322A6 antibody in VEGFR-2 signal transduction is not very strong. However, when treated 322A6 conjugated with Romidepsin (c45-ADC), the relative cell viability of HUVEC is dropped significantly. Not to be limited by theory, it is believed that the drop of relative cell viability of HUVEC is resulted from the cytotoxicity of the ADC of 322A6 antibody instead of from the inhibition of HUVEC proliferation.

Chimeric Antigen Receptor T-Cell (CAR-T) Immunotherapy

Peripheral blood mononuclear cells (PBMCs) were isolated from healthy donors and stimulated with Dynabeads® Human T-Activator CD3/CD28 (Gibco) in RPMI with 10% FBS (hyclone) and 100 U/mL recombinant interleukin-2 (Roche) for 48 hr. Activated T cells were collected using the Pan T-Cell Isolation Kit, human (Miltenyi Biotec) according to the manufacturer's protocol. Lentiviral vector contained the single-chain variable fragment of anti-VEGFR-2 antibody, and the signaling domains of 4-1BB and CD3-z. Viral supernatants were produced by transient transfection of HEK293T cells with the transfer genome plasmid and lentiviral packaging helper plasmids pMD2.G and pCMVΔR8.91 and used to transduce human T cells on RetroNectin-coated plates (TaKaRa Bio Inc.). Transduction efficiency was analyzed by flow cytometry.

The result is shown in FIG. 12. The quantification analysis shows that 5.1%, 10.4% and 7.79% of 1121, 12A6 and 322A6 CAR expressed on the T cells, respectively.

Cytotoxicity Assay of Antigen Receptor T-Cell

Cytotoxic activity was measured by using the Cytotoxicity Detection Kit (Roche, Indianapolis, Ind., USA) according to the manufacturer's instructions. Anti-VEGFR-2 CAR T cells were incubated with the VEGFR2 positive cell lines at the indicated E:T ratios for 16 hr at 37° C. Percent-specific cytolysis was calculated by using the formula: (Test-effector control-low control/high control-low control)*100. High control is calculated after incubating target cells in 1% Triton X 100; effector control is the spontaneous LDH release value of T cells alone; low control is the spontaneous LDH release value of target cells alone. Effector cells: primary T cell transduced with anti-VEGFR-2 CAR (5 days post 1st transduction). Target cells: FS293 (overexpressed VEGFR-2). Effector cells and target cells were co-cultured for 16 hours.

A scFv fragment of CD19 was also used for manufacturing a CAR-T as a control (CD19). T cell only was also taken as a control (T). 1121 antibody was a known anti-VEGFR-2 antibody that specifically binds to domains 2 and 3 of the VEGFR-2, which domains are far away from the cell membrane in the VEGFR-2. CAR-T of 1121 was used in the assay for comparison. The result is shown in FIG. 13. The CAR-Ts of 12A6 and 322A6 both have stronger cytotoxicity than the CAR-T of 1121. Not to be limited by theory, it is believed that 12A6 and 322A6 antibodies specifically bind to domains 6 and/or 7 of the VEGFR-2, which are near the cell membrane in the VEGFR-2.

Producing Radioactive-, Iodine-Bound Antibody

One ml of 25 mM Tris-HCl (pH7.5) and 0.4 M NaCl buffer solution was added to an IODO-gen tube, and then discarded. One hundred μl of buffer solution was added to the tube, and then 1 μl of I-123 or I-131 was added for reacting at room temperature for 6 minutes with gently shaking. The anti-VEGFR-2 antibodies were added for reacting at room temperature for 6 to 9 minutes with gently shaking. The reaction was terminated by transferring the reactants into a new eppendorf tube. The efficiency of the labeling process was analyzed by Radio-TLC with the developing solution of 85% methanol and ITLC/SG paper.

The efficiency of the labeling process $^{131}$I-anti-VEGFR-2-clone 45(322A6) is shown in FIG. 14. More than 96.8% of antibodies were labeled.

Stability of Radioactive Iodine-Bound Antibody in Serum

The labeled antibodies and serum derived from human or rat were mixed with the volume ratio of 1:19 and reacted at 37° C. At hour 0.25, 0.5, 1, 4, 8, 24, 48, and 72, 800 μl of 10% TCA was added to 10 μl of the sample and mixed. Proteins contained in the sample were precipitated by ice bath for 15 minutes. The supernatant was filtered with 0.45 μm PVDF membrane and the ratio-activity of the liquid was counted presenting the dissociated I-131. Stability=(activity before filtration−activity after filtration)/activity before filtration.

The result is shown in Table 8 revealing that $^{131}$I-anti-VEGFR-2-clone-45 does not degraded in serum in 72 hours.

TABLE 8

Radio-bound stability of $^{131}$I-antiVEGFR-2-c45 in human and rat serum, %

| Time (hr) | Human serum | Rat serum |
|---|---|---|
| 0 | 95.06 ± 0.59 | 89.95 ± 7.08 |
| 0.25 | 94.51 ± 0.68 | 91.67 ± 5.89 |
| 0.5 | 94.54 ± 0.58 | 93.11 ± 4.58 |
| 1 | 93.59 ± 0.68 | 92.52 ± 5.16 |
| 4 | 94.54 ± 0.66 | 93.56 ± 4.41 |
| 8 | 94.61 ± 0.67 | 93.65 ± 4.29 |
| 24 | 94.47 ± 0.49 | 93.21 ± 4.64 |
| 48 | 94.33 ± 0.64 | 93.06 ± 4.75 |
| 72 | 94.38 ± 0.61 | 93.17 ± 4.59 |

Detecting Tumor with Radioactive Iodine-Bound Antibody

SPECT/CT was utilized for detecting tumor with the radio-bound antibody according to the invention. The HT-29 xenografted mice were i.v. injected with 4 to 8 g μCi/μg of radio activity. Each mouse was administrated with 1 to 2 mg/kg B.W. $^{131}$I or $^{123}$I labeled anti-VEGFR2 antibody. At hour 1, 4, 24, and 48, the mice were scanned with SPECT/CT.

Figure 15:
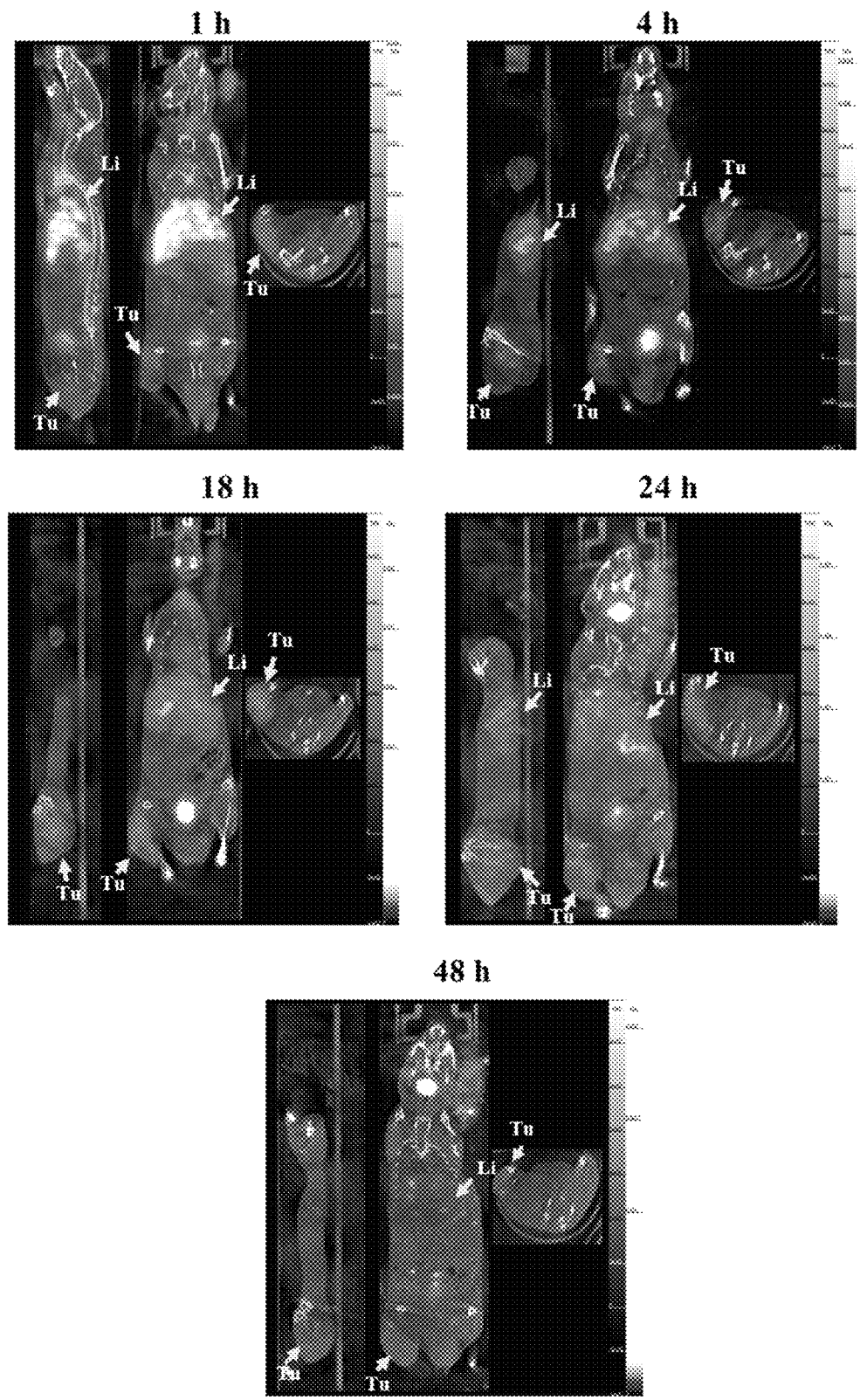
FIG. 15 shows the result of tumor detection in Nano-SPECT/CT of HT-29 xenografted mice by the radio-labeled antibody according to the invention.

The result is shown in FIG. 15. The result reveals that the radio-bound antibody 322A6 is able to specifically bind to the HT-29 xenografted tumor and the radioactive signal is accumulated in the tumor. The strongest signal appears at hour 18 in the tumor. The antibodies are degraded after hour 18, and almost all antibodies are degraded after hour 48.

Combination Therapy

Male B6 (C57BL/6JNarl) mice, aged 6 to 8 weeks old, were taken as the animal model. The mice were fed under a 12-hr light/dark cycle and received ad lib access to PMI feeds (RMH3000-5P76) and water. The mice were grouped as:

Group 1: IgG (Mu) (nonfunctional IgG antibody), 15 mpk/i.v., twice/week, n=6
Group 2: αCTLA-4 (Mu), 5 mpk/i.v.+IgG (Mu), 10 mpk/i.v., twice/week, n=6
Group 3: αCTLA-4 (Mu), 5 mpk/i.v.+322 A6, 10 mpk/i.v., twice/week, n=6
Group 4: IgG (Mu), 5 mpk/i.v.+322 A6, 10 mpk/i.v., twice/week, n=6

The tumor sizes were measured and listed in Table 9. The combination of anti-CTLA4 antibody and anti-VEGFR-2 antibody (322A6) has synergistic effect.

TABLE 9

| Tumor volume (mm³) | Day 0 | Day 4 | Day 7 | Day 11 | Day 14 | Day 21 |
|---|---|---|---|---|---|---|
| IgG (Mu), 15 mpk | 0.0 | 0.0 | 30.9 | 195.3 | 866.2 | 3540.5 |
| αCTLA-4 (Mu) 5 mpk + IgG (Mu)10 mpk | 0.0 | 0.0 | 5.4 | 211.0 | 634.6 | 2425.5 |
| αCTLA-4 (Mu) 5 mpk + 322A6 10 mpk | 0.0 | 0.0 | 12.7 | 86.9 | 365.0 | 1140.3 |
| IgG(Mu) 5 mpk + 322 A6 10 mpk | 0.0 | 0.0 | 3.0 | 174.7 | 739.5 | 3240.9 |

The body weights were also measured and listed in Table 10, and it reveals that the body weights of all the groups are substantially the same.

TABLE 10

| Body Weight (gm) | 0 day | 4 day | 7 day | 11 day | 14 day | 21 day |
|---|---|---|---|---|---|---|
| IgG (Mu), 15 mpk | 25.1 | 26.2 | 26.2 | 26.1 | 26.1 | 31.7 |
| αCTLA-4 (Mu) 5 mpk + IgG (Mu)10 mpk | 25.0 | 25.0 | 25.8 | 25.6 | 25.5 | 28.7 |
| αCTLA-4 (Mu) 5 mpk + 322A6 10 mpk | 25.6 | 25.6 | 26.2 | 26.2 | 26.1 | 28.2 |
| IgG(Mu) 5 mpk + 322 A6 10 mpk | 25.4 | 25.4 | 26.4 | 26.2 | 26.8 | 31.8 |

Humanization of Antibody

Selection of human V region framework: Sequences selection of human V region framework sequences human germ-line $V_L$ and $V_H$ sequences with the highest degree of homology with the 322A6 framework regions were identified from IMGT database (http://www.imgt.org/) and commonly used VH3/Vk1(4D5). Finally, framework sequences of VH3 and Vk1 were selected for the VH framework and the VL framework, respectively. Humanized framework marked as Hu was come from IMGT database and Hd series were from 4D5 framework.

Full length CDR grafted Ab Construction: 322A6 (HH) consisted complete human framework (VL κ subgroup I and $V_H$ subgroup III) with the six complete murine CDR sequences. The 322A6(HH) and half humanized (MH or HM) antibody construct were assembled by PCR and restriction enzyme digestion for directional sub-cloning into modified antibody expression vector pTCAE8.3. The plasmid contains a DNA fragment encoding human kappa light-chain and human IgG1 C region. The full length antibody was expressed in Free-style 293 cells.

Back mutation: Clone 322A6(HuB1-Hd) was selected for 1-3 run back mutation from CDR grafted framework for binding activity recovery. Briefly, we perform analysis CDR grafting framework by computer modeling that to examine by a 5 Å proximity, upper core region, interface area and also apply previous experience of most commonly used in successful cases. We had selected 3 run, that 5~11 possible amino acid back mutation. These sites were recognized as important sites for CDR binding and structure. After cloning and antibody expression, binding activity was determined by ELISA and BIAcore. The combination clone of heavy chain (HuB1) and light chain (Hd) with 7 amino acid back mutation (7+0) was the suitable candidate for VEGFR2 binding.

A humanized antibody Hu322B1HdH was constructed with a heavy chain variable region comprising the amino acid sequences of SEQ ID NO: 25 and a light chain variable region comprising the amino acid sequence of SEQ ID NO: 27. The heavy chain variable region is encoded by a nucleic acid sequence of SEQ ID NO: 24 and the light chain variable region is encoded by a nucleic acid sequence of SEQ ID NO: 26. The alignment of $V_L$ segments is shown in FIG. 16, and the alignment of $V_H$ segments is shown in FIG. 17.

While the present invention has been described in conjunction with the specific embodiments set forth above, many alternatives thereto and modifications and variations thereof will be apparent to those of ordinary skill in the art. All such alternatives, modifications and variations are regarded as falling within the scope of the present invention.

What is claimed is:

1. An antibody or antigen-binding fragment thereof that specifically binds to an epitope in human vascular endothelial growth factor receptor 2 (VEGFR-2) or a fragment thereof; wherein the human vascular endothelial growth factor receptor 2 has the amino acid sequence of SEQ ID NO: 1, and the epitope comprises:

the serine residue at position 711, the lysine residue at position 716, the aspartic acid residue at position 717, and the arginine residues at positions 725 and 726 of SEQ ID NO: 1; which antibody or antigen-binding fragment thereof comprises complementarity determining regions (CDRs) of a heavy chain variable region and complementarity determining regions of a light chain variable region, wherein the complementarity determining regions of the heavy chain variable region comprises CDRH1, CDRH2 and CDRH3 regions, and the complementarity determining regions of the light chain variable region comprises CDRL1, CDRL2 and CDRL3 regions, and the CDRH1 region comprises the amino acid sequence of SEQ ID NO: 4; the CDRH2 region comprises the amino acid sequence of SEQ ID NO: 5; the CDRH3 region comprises the amino acid sequence of SEQ ID NO: 6; the CDRL1 region comprises the amino acid sequence of SEQ ID NO: 7; the CDRL2 region comprises the amino acid sequence of SEQ ID NO: 8; and the CDRL3 region comprises the amino acid sequence of SEQ ID NO: 9.

2. The antibody or antigen-binding fragment thereof according to claim 1, which is a mammalian antibody.

3. The antibody or antigen-binding fragment thereof according to claim 1, which comprises a heavy chain variable region comprising the amino acid sequence of SEQ ID NO: 17; and a light chain variable region comprising the amino acid sequence of SEQ ID NO: 19.

4. The antibody or antigen-binding fragment thereof according to claim 3, wherein the heavy chain variable region is encoded by a nucleic acid sequence of SEQ ID NO: 16; and the light chain variable region is encoded by a nucleic acid sequence of SEQ ID NO: 18.

5. The antibody or antigen-binding fragment thereof according to claim 1, which comprises a heavy chain variable region comprising the amino acid sequence of SEQ ID NO: 25; and a light chain variable region comprising the amino acid sequence of SEQ ID NO: 27.

6. The antibody or antigen-binding fragment thereof according to claim 5, wherein the heavy chain variable region is encoded by a nucleic acid sequence of SEQ ID NO: 24 the light chain variable region is encoded by a nucleic acid sequence of SEQ ID NO: 26.

7. The antibody or antigen-binding fragment thereof according to claim 1, which is conjugated with a therapeutic agent.

8. The antibody or antigen-binding fragment thereof according to claim 7, wherein the therapeutic agent is selected from the group consisting of antimetabolites, alkylating agents, alkylating-like agents, DNA minor groove alkylating agents, anthracyclines, antibiotics, calicheamicins, antimitotic agents, topoisomerase inhibitors, HDAC inhibitor, proteasome inhibitors, and radioisotopes.

9. The antibody or antigen-binding fragment thereof according to claim 1, which is expressed on a surface of a cell.

10. The antibody or antigen-binding fragment thereof according to claim 9, wherein the cell is a T-cell.

* * * * *